(12) United States Patent
Kurihashi

(10) Patent No.: US 6,238,363 B1
(45) Date of Patent: May 29, 2001

(54) APPARATUS FOR INTUBATION OF LACRIMAL DRAINAGE PATHWAY

(75) Inventor: Katsuaki Kurihashi, Hamamatsu (JP)

(73) Assignee: MLC Limited Company (JP)

(*) Notice: Subject to any disclaimer, the term of this patent is extended or adjusted under 35 U.S.C. 154(b) by 0 days.

(21) Appl. No.: 09/256,232

(22) Filed: Feb. 24, 1999

(30) Foreign Application Priority Data

Aug. 27, 1998 (JP) .................................................. 10-256109

(51) Int. Cl.[7] ........................................................ A61M 5/00
(52) U.S. Cl. ............................. 604/8; 604/294; 606/107; 606/198
(58) Field of Search .................................. 604/8–10, 289, 604/294; 623/4; 606/107, 191, 198, 199

(56) References Cited

U.S. PATENT DOCUMENTS

| | | | |
|---|---|---|---|
| 5,334,137 | * | 8/1994 | Freeman ..................... 604/8 |
| 5,417,651 | * | 5/1995 | Guena et al. ............................. 604/8 |
| 5,769,093 | * | 6/1998 | Bays ........................................ 604/8 |
| 5,830,171 | * | 11/1998 | Wallace ................... 604/8 |
| 5,868,697 | * | 2/1999 | Richter et al. ........................... 604/8 |
| 6,027,470 | * | 2/2000 | Mendius ................................... 604/8 |

* cited by examiner

*Primary Examiner*—John G. Weiss
*Assistant Examiner*—David J. Cho
(74) *Attorney, Agent, or Firm*—Lorusso & Loud

(57) ABSTRACT

A device for intubation of a lacrimal duct is inserted into the lacrimal duct, having a smaller diameter tube or rod portion, and a larger diameter tube which is connected with one end of the smaller diameter portion, and a stopper which consists of a plug, brim, ring, etc., attached to the other end of the smaller diameter tube or rod. The tip of the larger diameter tube is a closed end.

20 Claims, 39 Drawing Sheets

F I G. 2
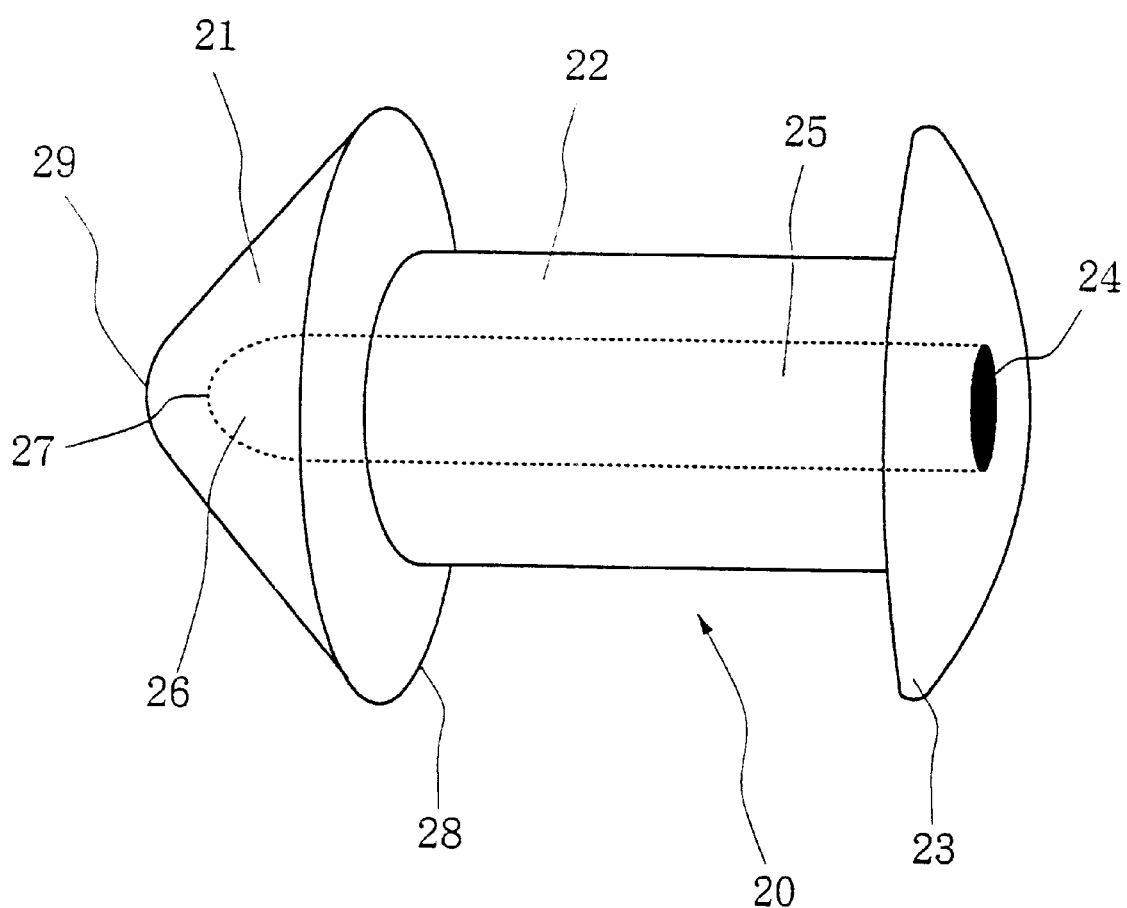

APPARATUS FOR INTUBATION OF LACRIMAL DRAINAGE PATHWAY

TECHNICAL BACKGROUND

This invention relates to an apparatus for intubation of the lacrimal duct (lacrimal drainage pathway) for treatments of lacrimal duct obstruction and dry eye.

As shown in FIG. 1, the lacrimal gland 14 secrete tears which drain into the inferior nasal meatus 18 via the lacrimal duct after moistening the ocular surface 17 having the cornea 15 and conjunctiva 16. The lacrimal duct consists of the upper punctum 1, lower punctum 2, vertical portion of the upper punctum 3, vertical portion of the lower punctum 4, boundary portion between the upper vertical and horizontal portions 5, boundary portion between the lower vertical and horizontal portions 6, upper horizontal portion 7, lower horizontal portion 8, common canaliculus 9, internal common punctum 10, lacrimal sac 11, nasolacrimal duct 12. The lower end 13 of the nasolacrimal duct 12 opens into the inferior nasal meatus 18.

In patients with dry eye having hypofunction of the lacrimal gland and deficiency of tears, tears which are very important for the eye immediately drain away via the lacrimal duct.

To suppress the tear drainage, occlusion of the upper punctum 1 and/or lower punctum 2 using electric cautery is performed. Occlusion using a punctal plug (mentioned later) inserted into the upper punctum 1 and lower punctum 2 is also performed.

By blocking the upper punctum 1 and lower punctum 2 like this, tears are accumulated in the conjunctival sac and dry eye symptoms disappear in many cases.

Dry eye symptoms include asthenopia, waking irritation, grittiness, foreign body sensation, scratchiness, soreness, difficulty to open the eyes in an air conditioned room, injection, burning and so on.

Recently, aggravation of dry eye symptoms by spending time in front of a monitor has become a problem. This is due to the fact that evaporation of tears is accelerated in individuals with tear deficiency by decreased frequency of blinking which is induced by looking at a monitor.

Artificial tears are added as eyedrops in another treatment of dry eye. But the ingredients of artificial tears are far from those of natural tears. It is best for eye to be wet with natural tears. Therefore, the treatment of punctal occlusion is superior.

Unlike artificial tears, tears contain lysozyme, lactoferrin, immunoglobulin, and so on which protect eye from bacteria and viruses. And some artificial tears contain a preservative which is harmful to the eye.

The roles of tears include an optical role wherein tears make smooth the microscopically irregular surface of the cornea 15 to improve eyesight, a role of lubricant wherein tears act as lubricant and the movements of eyelids become smooth, and other roles. Artificial tears can not be expected to play these various roles.

Therefore, occlusion of the upper punctum punctum 1 and/or lower punctum 2 to wet the eye with natural tears is superior. But punctal occlusion by argon laser may induce epiphora postoperatively. In such a case, punctal and canalicular surgery are needed to reconstruct canaliculi and puncta.

The use of a punctal plug is superior because a punctal plug can be removed easily in such cases.

In 1975 Freeman reported a punctal plug as shown in FIG. 2 for the treatment of dry eye. For example, see Freeman, J M: The punctum plug: evaluation of a new treatment for the dry eye. Trans Am Acad Ophthalmol Otolaryngol 79: op 874–879, 1975.

The punctal plug shown in FIG. 2 consists of the tip 21, shaft 22, brim 23 and there is a hole 24 in the center of brim 23. The hole 24 is continuous with a tubular lumen 25 of shaft 22 and the lumen 26 with a closed end 27 of the tip 21. The punctal plug shown in FIG. 2 measures 2.8 mm in total length, 1.5~2.0 mm in diameter of brim, 0.7 mm in height of brim, 1.5 mm in length of shaft and 0.7 mm in diameter of shaft.

The punctal plug in FIG. 2 is used as shown in FIG. 3. The punctal plug is inserted into puncta 1, 2 and vertical portion of canaliculus 3, 4, and the total length of the puncta 1, 2 and vertical portions of canaliculus 3, 4 is 2.5 mm on the average. Therefore, the total length 2.8 mm of the punctal plug is too long. Consequently, the brim 23 touches the cornea 28 and not infrequently induces a foreign body sensation.

FIG. 4 shows a punctal plug of the FCI company. This is also used for the treatment of dry eye in Japan. For example see, Junzo Hirano & Miki Hirano: Experience of the treatment for a case with Stevens-Johnson syndrome with severe keratoconus, Japanese Review of Clinical Ophthalmology 91:41–44, 1997.

The punctal plug in FIG. 4 is a miniaturized one. This punctal plug measures 1.7 mm in total length, 1.5 mm in diameter of brim 23, and is miniaturized as a whole. It measures 0.1 mm in thickness of brim 23 which inclines 20° against the shaft 22.

The Punctal plug in FIG. 4 also consists of tip 21, shaft 22 and brim 23, and as in the punctal plug as shown in FIG. 2, hole 24 is continuous with the lumen 25 with closed end 27 of shaft 25.

In use, the tip 29 of the punctal plug is pushed into the lacrimal duct to or near the boundary portion 5, 6 between the vertical portion 3, 4 and horizontal portion 7, 8 of canaliculus, by a metal probe which is inserted through the hole 24 to the closed end 27.

FIG. 5 shows a punctal plug with a tapered shaft form. This plug is also miniaturized and consists of the tip 21, shaft 22 and brim 23. As in the punctal plug shown in FIG. 2, the hole 24 is continuous with lumen 25 with a closed end 27 of the shaft 22. The shaft 22 becomes gradually smaller as it tapers toward the brim 23.

Although corneal disorder is hardly induced by such a miniature punctal plug, the miniature punctal plug can migrate into the horizontal portion of canaliculus 7, 8 as shown in FIG. 6, and as shown in FIG. 7 into the lacrimal sac 11 and nasolacrimal duct 12, resulting in canaliculitis and dacryocystitis which sometimes need surgical intervention (For example, see Rumelt S et al: silicone punctal plug migration resulting in dacryocystitis and canaliculitis. Cornea 16: 377–399, 1997.).

Let us do a little more explanation in this respect. For dry eye, punctal plugs are inserted into puncta and left in place as shown in FIG. 3. But the punctal plug is apt to move because of the shallow insertion.

And as shown in FIG. 6, 7, the punctal plug can migrate into the lacrimal duct.

Furthermore, as shown in FIG. 2, FIG. 4 and FIG. 5, the edges of the tip 29 of either punctal plug are angular and sometimes stimulate canaliculus, resulting in the growth of pyogenic granuloma (For example, see Rapoza P A & Ruddat M S: Pyogenic granuloma as a complication of silicone punctal plug. Am J Ophthalmol 113: 454–455, 1992).

Stimulation by the tip 29 of punctal plug sometimes induces canalicular obstruction between the vertical portion 3, 4 and horizontal portion of canaliculus (For example, see Fayet B et al: Stenoses canaliculaires compliquant la pose de bouchouns lacrimaux. Incidence et mecanismus, J Fr Ophthalmol 15: 25–33, 1992.)

Granuloma sometimes pushes the punctal plug out of the puncta.

On the other hand, FIGS. 8~10 show various nunchaku style silicone tubings which are invented by this inventor. For example, see U.S. Pat. No. 2,539,325.

The apparatus for intubation of the lacrimal duct shown in FIGS. 8~10 consists of smaller soft tube 40, 41 and larger tube 42, 43 of a certain length, and the ends 47, 48 of the larger tube are closed.

Smaller tube 40, 41 extends between two larger tubes 42, 43, and the middle point 44 of the smaller tube 40, 41 is marked.

The smaller soft tube 40, 41 is connected with the larger tubes 42, 43. Two millimeter end lengths of the smaller tube 40, 41 are inserted into the larger tubes 42, 43 for connection. Therefore, the jointed portions 45, 46 are 2 mm in length. The tips 47, 48 of the larger tubes are sharp pointed and closed. For example, 2 mm tips of the tube are completely sealed with silastic adhesive, and then diagonally cut to taper the closed ends 47, 48. Small cuts 49 are made in the larger tubes 42, 43 parallel to the tubes 42, 43.

The junctions 45 make steps (shoulders) in the case of FIG. 8. As shown in FIGS. 9~10, it is possible to make tapered junctions 51 without steps.

And in the cases shown in FIGS. 9~10, the ends 53, 54 of the larger tube are conical in shape.

In the devices of FIGS. 8~9, it is very rare for the junctions 45 to separate. However, FIG. 10 shows a one piece tube without any junctions which consists of the smaller tube 40, 41 and larger tubes 42, 43 is made from the first.

1) In prior methods of monocanalicular intubation using the half size nunchaku-style silicone tubing shown in FIGS. 8~10 or a silicone tube of uniform diameter over its total length, it is necessary to fix the tube at the puncta 1, 2 with suturing because such tubing lacks the brim.

2) Prior punctal plugs shown in FIGS. 2~7 are angular, and cause stimulation which sometimes induces granuloma.

3) Further, punctal plugs shown in FIGS. 2~7, sometimes cause canalicular obstruction between the vertical portion 3, 4 and the horizontal portion 7, 8 of the canaliculus.

4) The punctal plugs shown in FIGS. 2~8 also create a problem in that they sometimes migrate into the canaliculus, lacrimal sac and nasolacrimal duct because their brim is circular and too small.

5) Prior art nunchaku-style silicone tubings shown in FIGS. 8~10 are sometimes difficult to insert from the puncta 1, 2 because the closed ends are not sufficiently sharp pointed.

6) Prior art punctal plugs shown in FIGS. 2~7, sometimes come out because of their shallow insertion.

7) Dry eye symptoms are sometimes aggravated in patients with both dry eye and dacryocystitis, after intubation using prior art tubes shown in FIGS. 8~10 and/or dacryocystothinostomy.

8) Punctal plugs shown in FIGS. 2~7, are not stable.

9) Tubes with the same diameter over their total length are not stable even if a brim is attached to them.

10) Prior art tubes shown in FIGS. 8~10 sometimes induce slitting of the puncta 1, 2 and canaliculi 3–8, as shown in FIG. 11.

SUMMARY OF THE INVENTION

It is an object of the present invention to provide an apparatus for intubation of the lacrimal duct which is stable in the lacrimal duct, can be easily inserted into the lacrimal duct and be easily removed, is not in danger of movement after implantation and does not induce growth of granuloma.

It is another object of this invention to provide an apparatus for intubation of the lacrimal duct which can be used for reconstruction of the lacrimal duct where obstructions are present.

One embodiment of the present invention for intubation of the lacrimal duct is characterized by the presence of a smaller tube or rod, a prescribed length of larger tube which is joined with one end of the smaller tube or rod, and a stopper which is joined with the other end of the smaller tube or rod.

Another embodiment according to this invention is an apparatus for intubation of lacrimal duct which is characterized by presence of a prescribed length of larger tube and a stopper joined with the posterior end of the larger tube. The stopper may be a punctal plug, brim, ring and so on.

The present invention provides for the treatment of lacrimal duct obstruction and dry eye by providing a device for intubation of the lacrimal duct which can be used easily with decreased pain to patients, can be quickly and correctly inserted into the lacrimal duct, is not easily dislocated during the intubation period, and can be easily removed after completion of treatment.

This invention especially improves the stability of the device for intubation in the lacrimal duct.

In the present invention, an apparatus for intubation of the lacrimal duct includes a stopper. The stopper may be a punctal plug, brim, ring or other such structure.

Apparatus for intubation according to the present invention consists of a prescribed length of smaller tube or rod, a prescribed length of larger tube which is connected with one end of smaller tube or rod, and a punctal plug which is connected with the other end of smaller tube or rod.

In another embodiment, according to the present invention, the smaller tube or rod is omitted and the device consists of a prescribed length of the larger tube and the punctal plug which is connected with the posterior end of the larger tube.

Another embodiment of a device for intubation according to the present invention includes a brim, a prescribed length of smaller tube or rod, a prescribed length of larger tube which is connected with one end of the smaller tube or rod, and a brim which connected with the other end of the smaller tube or rod.

Yet another embodiment of a device for intubation according to the present invention includes a stopper, a prescribed length of smaller tube or rod, a prescribed length of larger tube which is connected with one end of the smaller tube or rod, the stopper being connected with the other end of the smaller tube or rod.

As stated above, use of punctal plug, brim or ring as a stopper brings about a great effect which each cannot be gained by the prior art.

In any said apparatus for intubation it is preferable that the tip of the larger tube is closed.

Furthermore, in a preferred embodiment of a device for intubation according to the present invention, its total length is 15~60 mm including tube and punctal plug, the punctal plug is 1.5~2.5 mm in length, the larger tube is 10~59 mm in length and the smaller tube is 1~5 mm in length.

In yet another embodiment of a device for intubation according to the present invention, a larger hard tube is connected with a punctal plug via a smaller soft tube.

In still another embodiment, the larger hard tube is directly connected with the punctal plug without intervention of the smaller soft tube.

In yet another embodiment of the present invention, various nunchaku-style silicone tubings are fixed to various punctal plugs with silastic adhesive.

In another embodiment of the present invention, a central segment is flexible and has both ends fixed to the punctal plug and tube with silicone adhesive. The punctal plug and tube are larger and harder, and the central segment constitutes has constitution to be able to pass through with forming a curve the boundary portion between the vertical and horizontal portions of canaliculus.

And the larger tube which is used in this invention has a closed end and a small cut is made in part of the tube to allow for insertion of a probe. This allows the apparatus to be easily inserted into the lacrimal duct.

In the punctal plug used in this invention, the brim is preferably 1.5~4.5 mm in diameter to prevent the punctal plug from migrating into the lacrimal duct, and simultaneously prevents tears from flowing into the puncta.

The apparatus for intubation of this invention has great stability in the lacrimal duct compared with the conventional punctal plug and, once in place, very rarely moves.

BRIEF DESCRIPTION OF THE DRAWINGS

FIG. 2 is a schematic diagram of a prior art punctal plug.

DETAILED DESCRIPTION OF THE EMBODIMENTS

Figure 1:
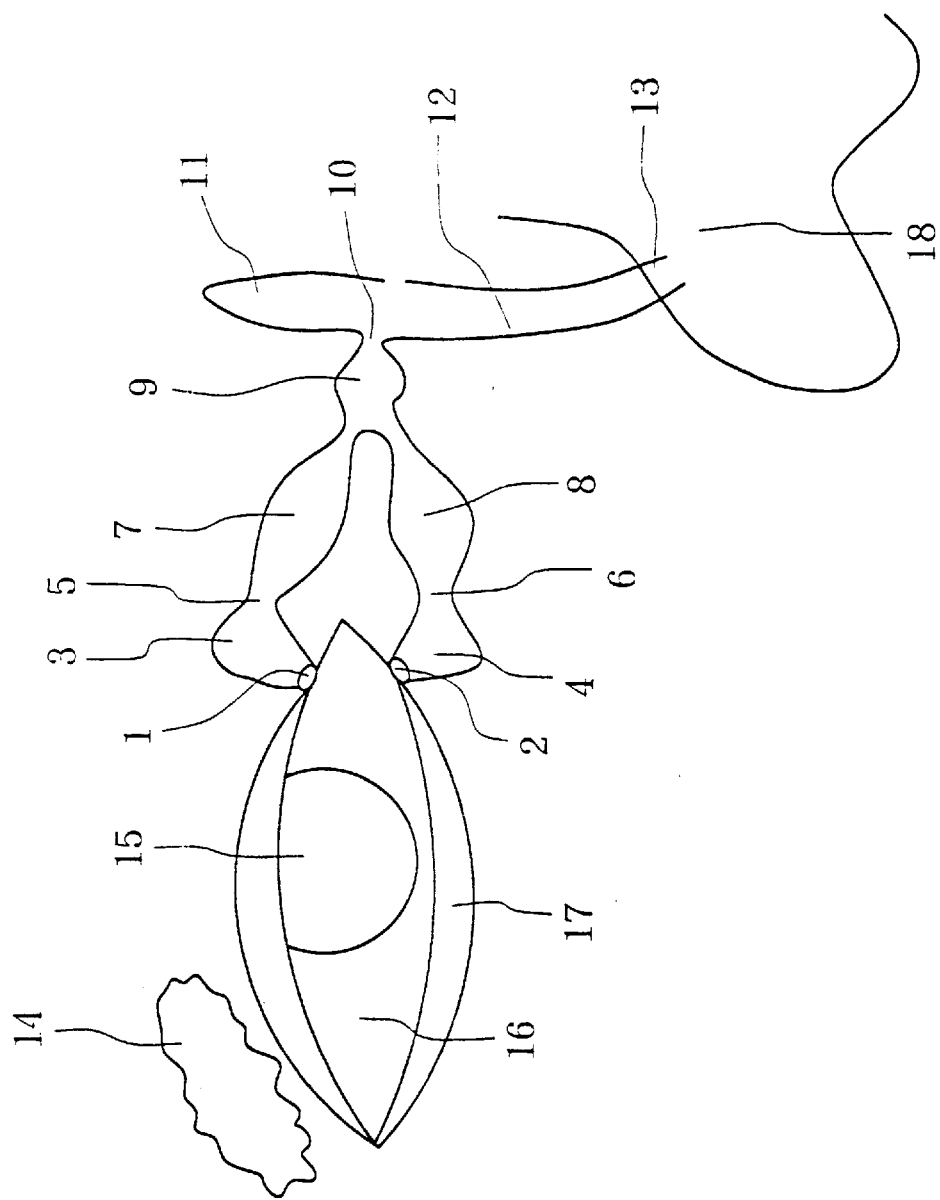
FIG. 1 is a schematic diagram of the lacrimal duct.
Figure 3:
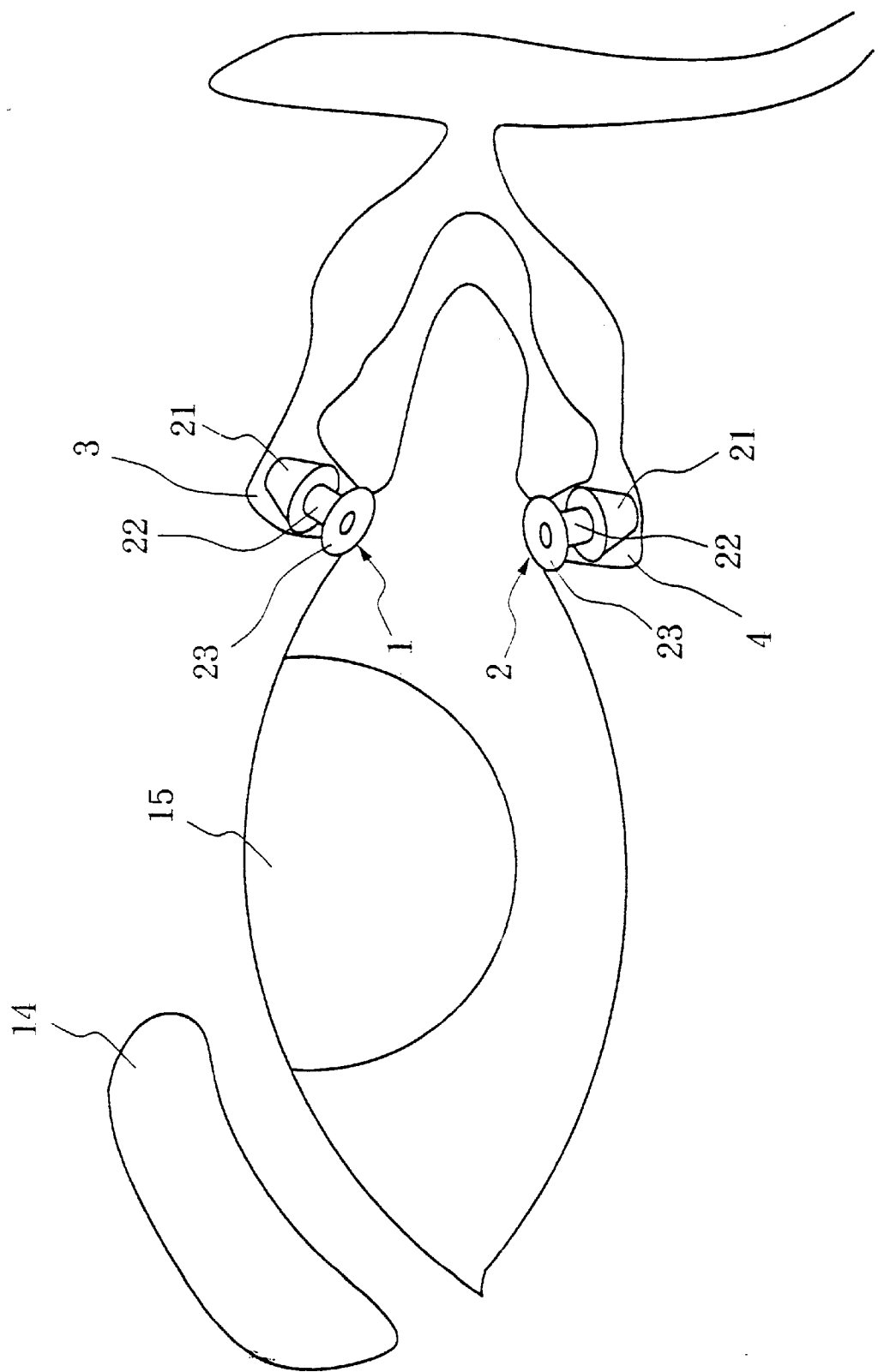
FIG. 3 is a schematic diagram showing how to use the punctal plug of FIG. 2.
Figure 4:
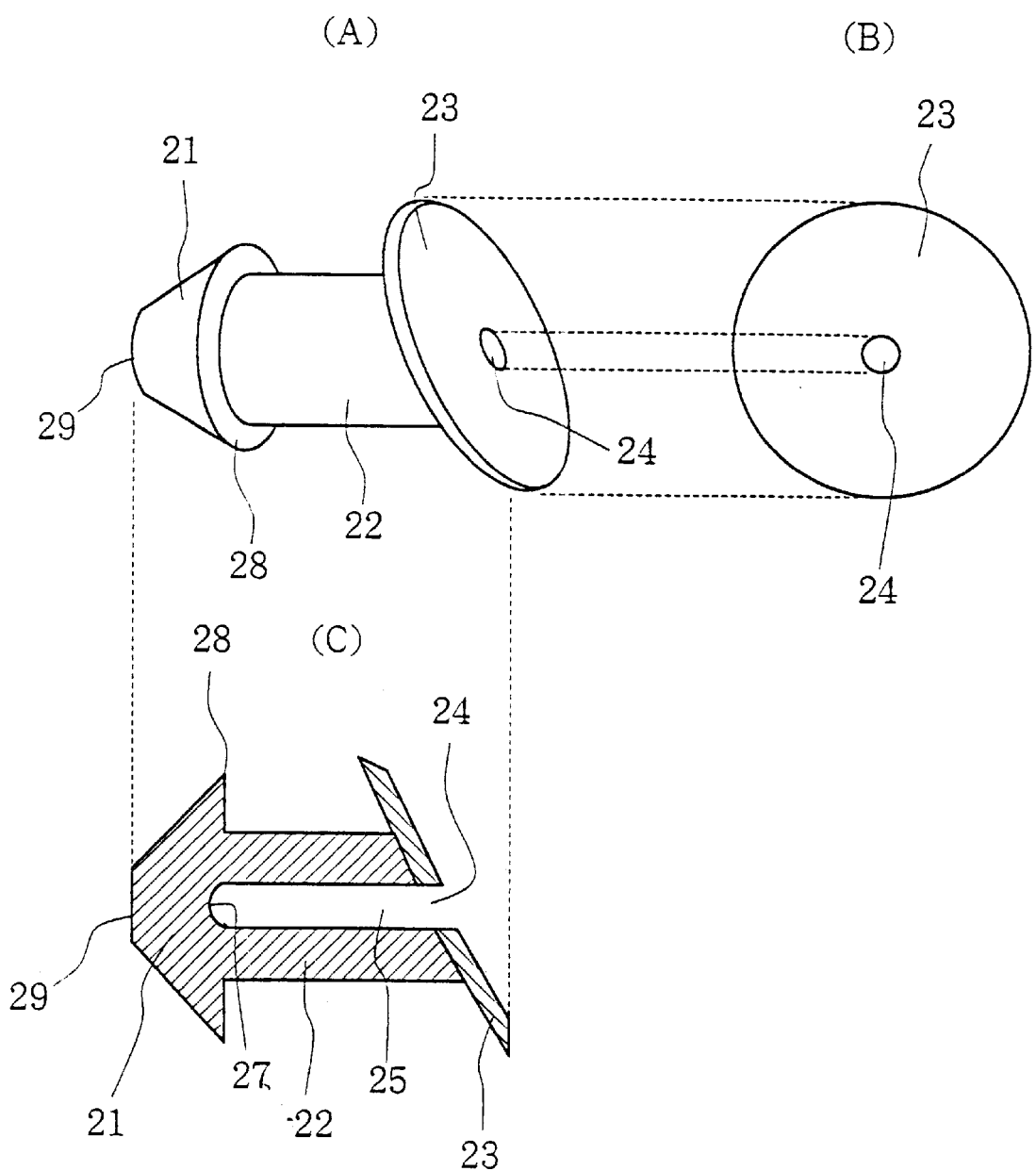
FIG. 4(A) is a schematic diagram showing another conventional plug.
FIG. 4(B) is the bottom view of the conventional plug of FIG. 4(A).
FIG. 4(C) is the mid-cross-sectional view of the conventional plug of FIG. 4(A).
Figure 5:
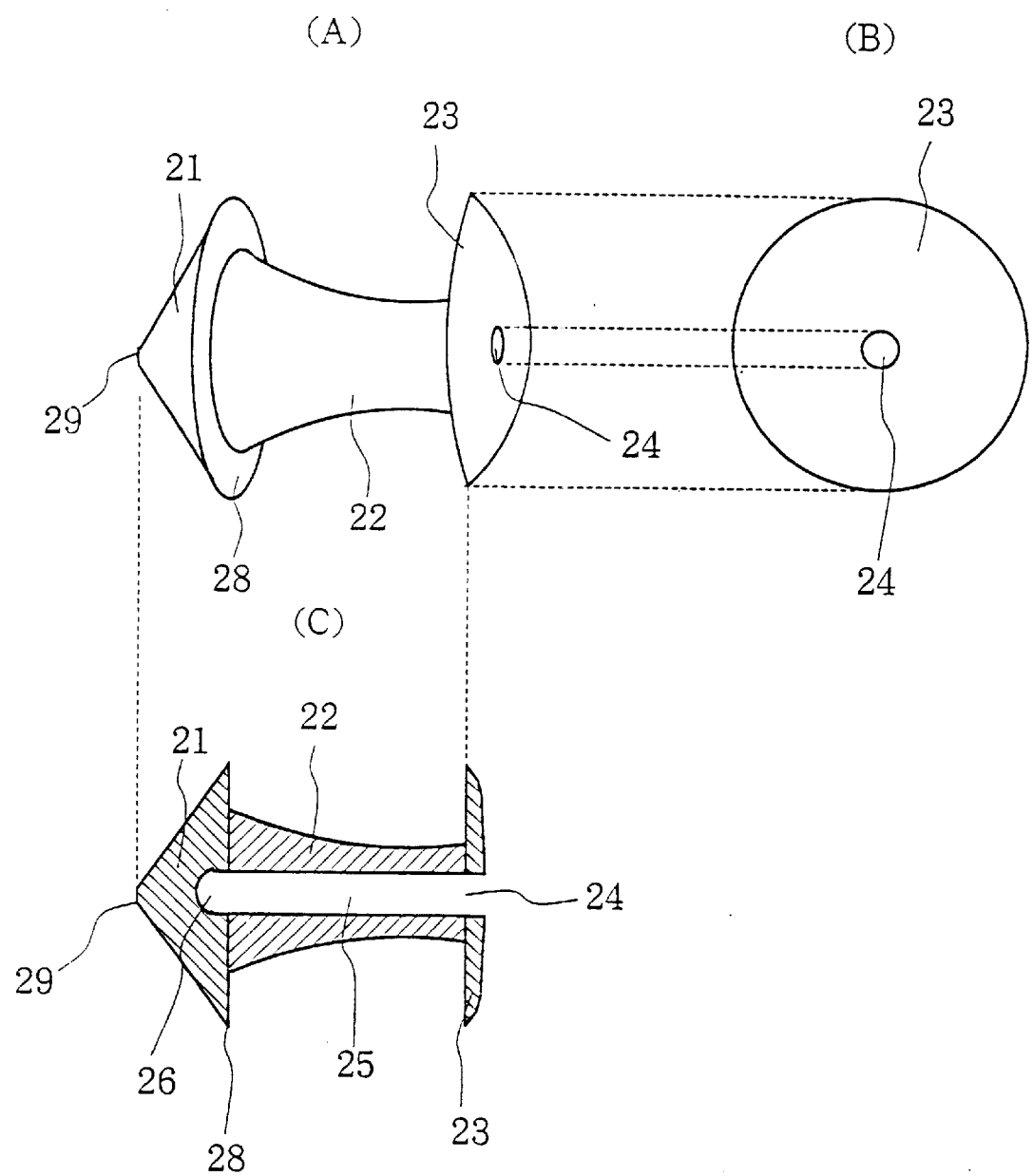
FIG. 5(A) is a schematic diagram showing another conventional punctal plug.
FIG. 5(B) is a bottom view of the conventional punctal plug of FIG. 5(A).
FIG. 5(C) is a mid-cross-sectional view of the conventional punctal plug of FIG. 5(A).
Figure 6:
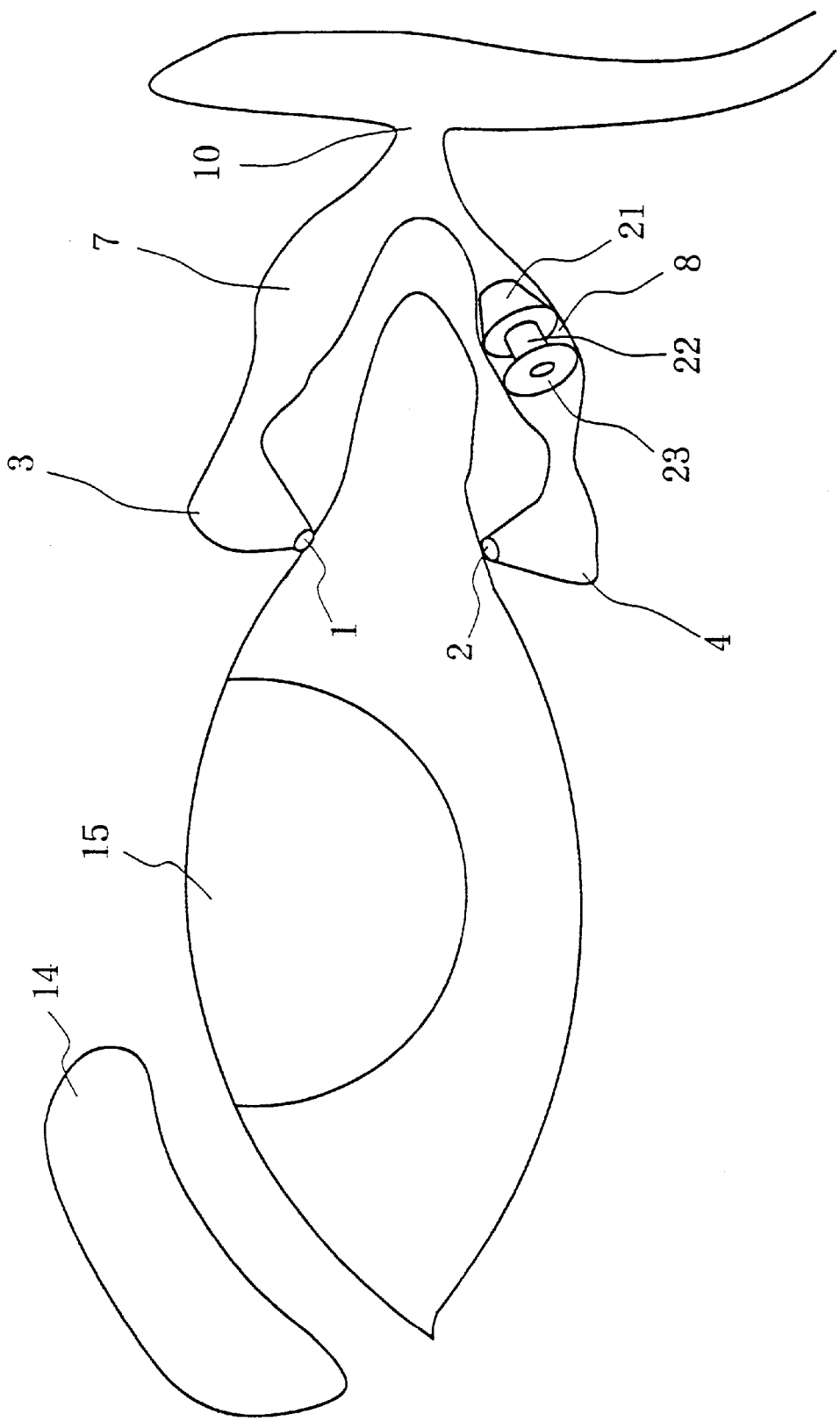
FIG. 6 is a diagram showing a failure of the plug of FIG. 2 in use.
Figure 7:
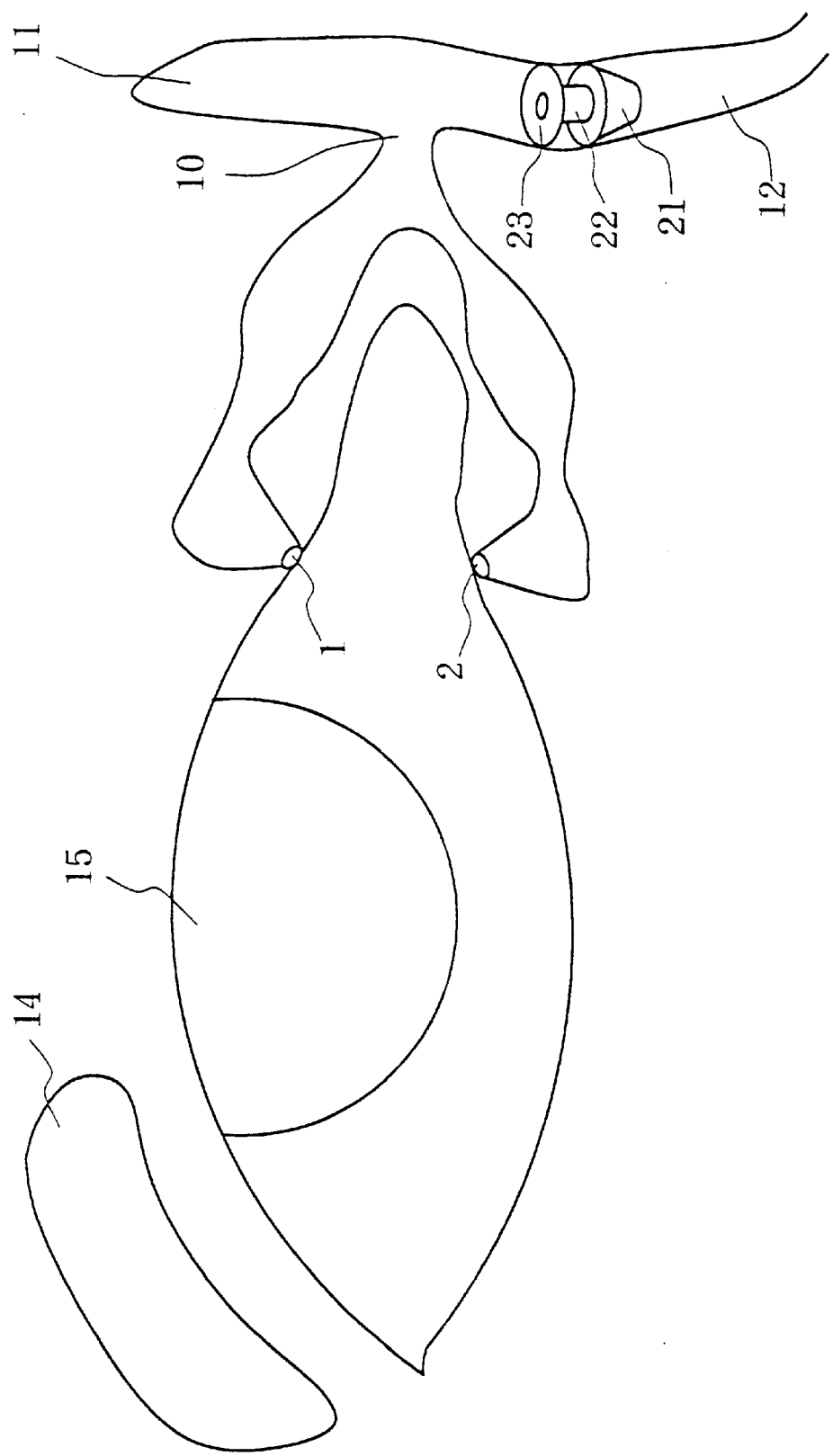
FIG. 7 is a diagram showing another failure of the plug of FIG. 2 in use.
Figure 8:
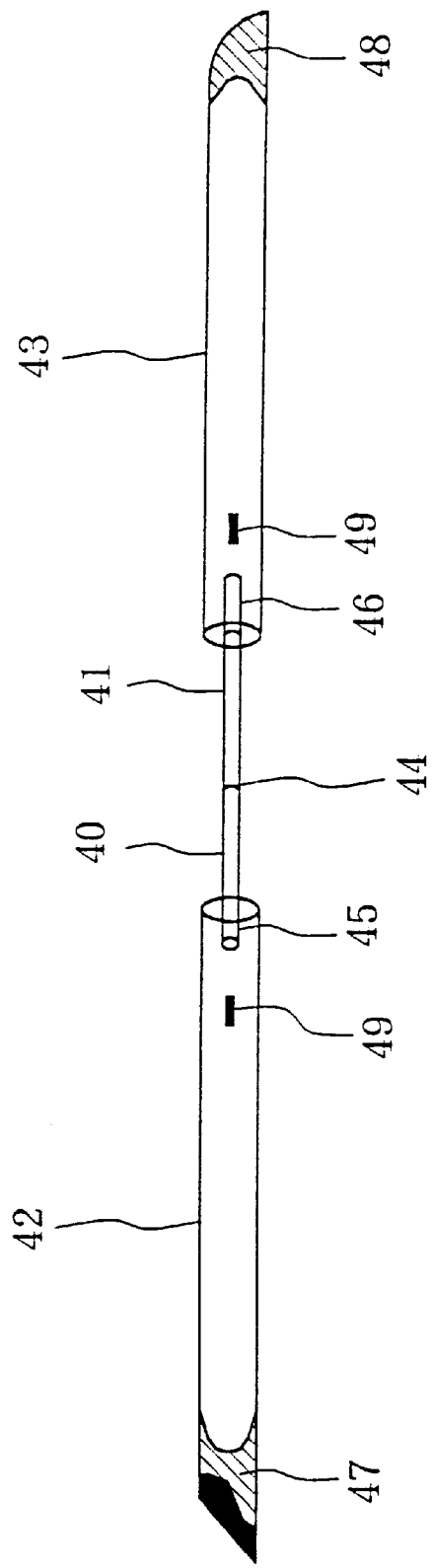
FIG. 8 is a diagram showing a conventional nunchaku-style silicone tubing.
Figure 9:
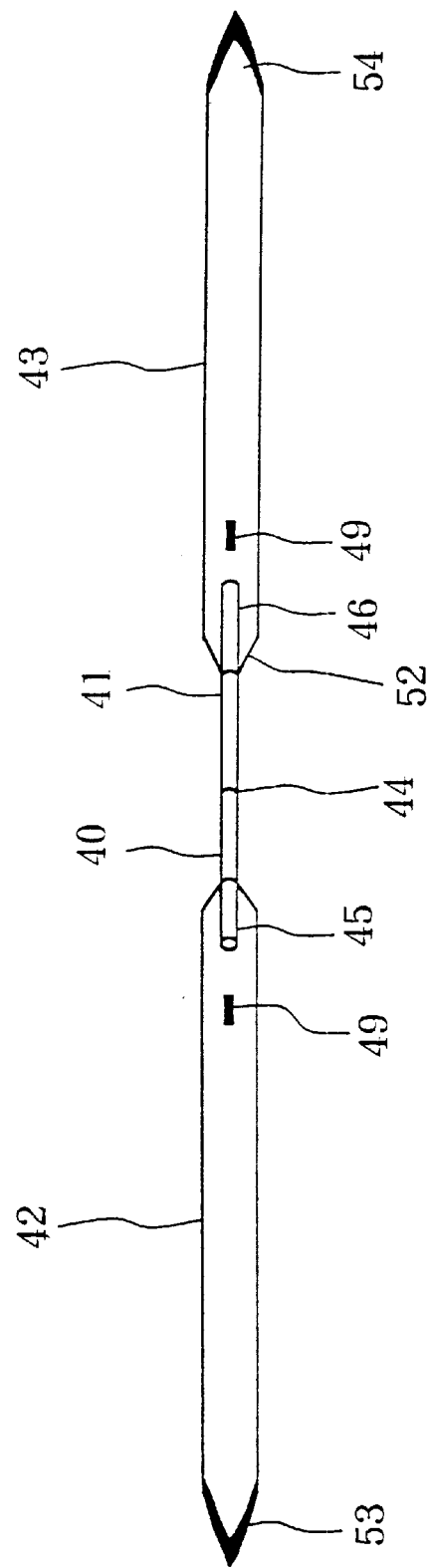
FIG. 9 is a diagram showing another conventional nunchaku-style silicone tubing.
Figure 10:
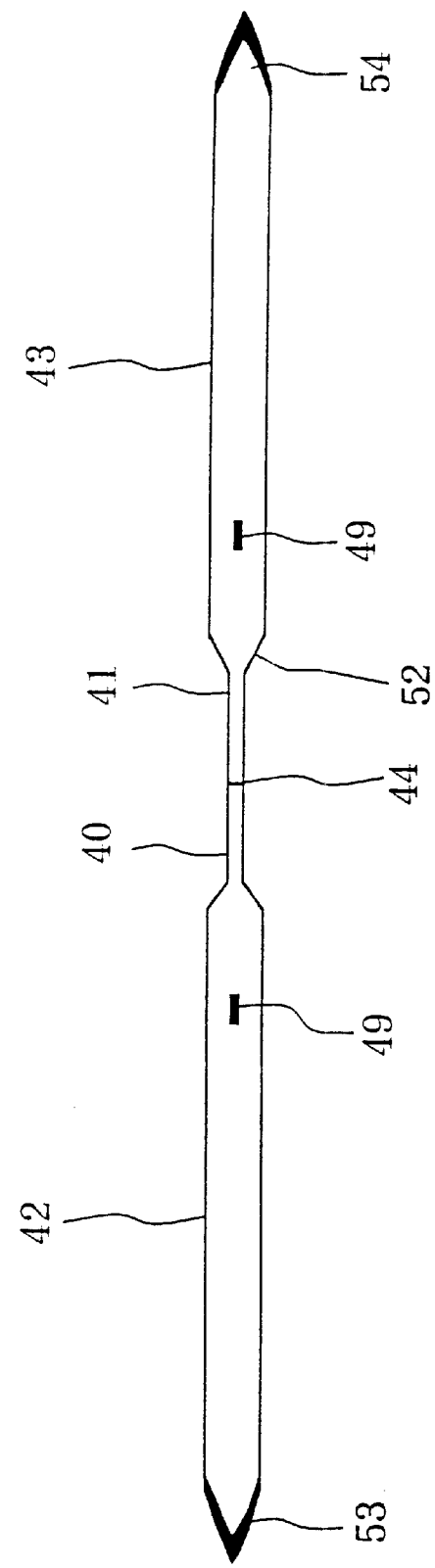
FIG. 10 is an explanatory diagram showing still another conventional nunchaku-style silicone tubing.
Figure 11:
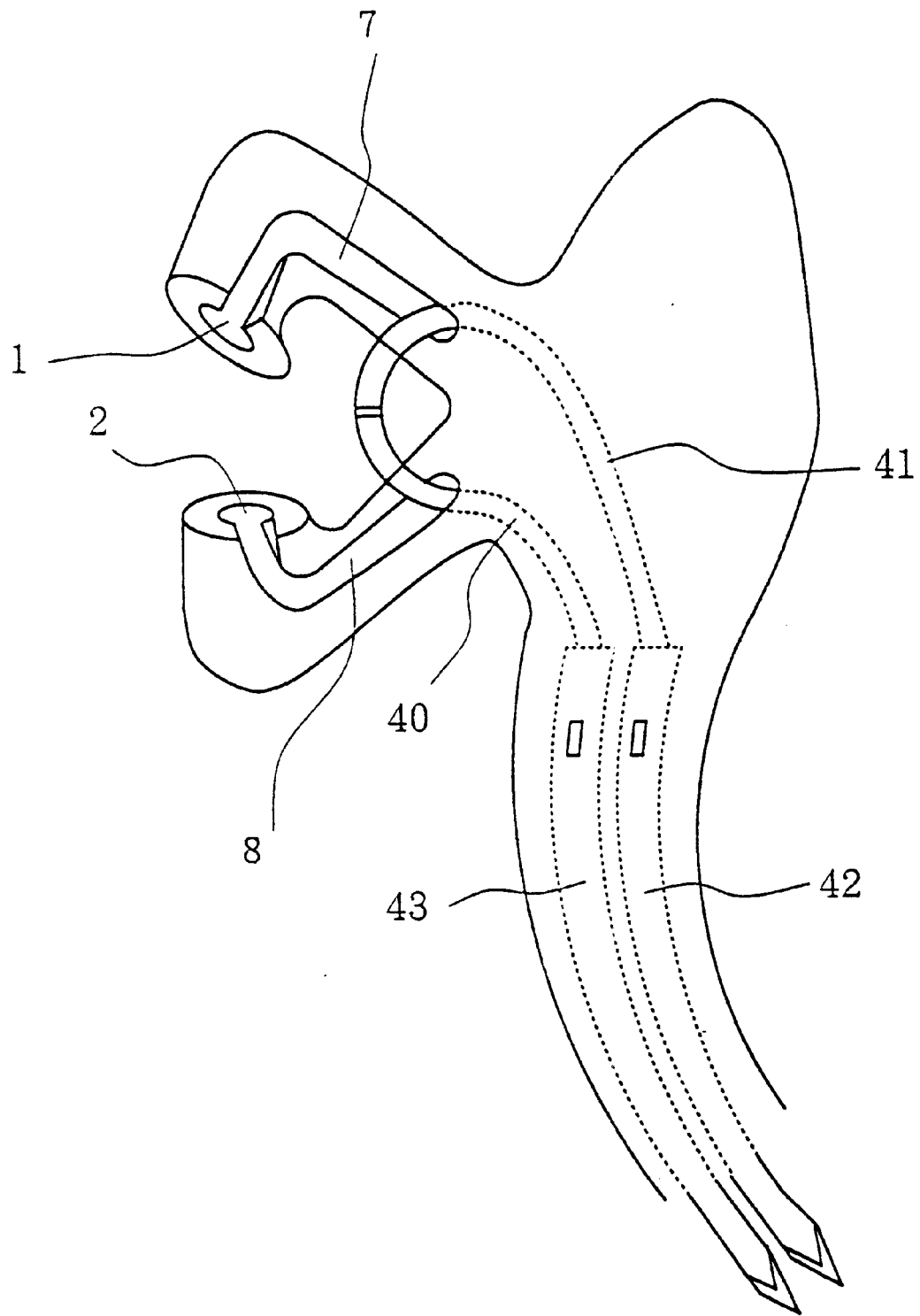
FIG. 11 is an explanatory diagram showing a failure in a conventional nunchaku-style silicone tubing.

Embodiments of this invention will now be explained, with reference to the drawing figures.

Figure 12:
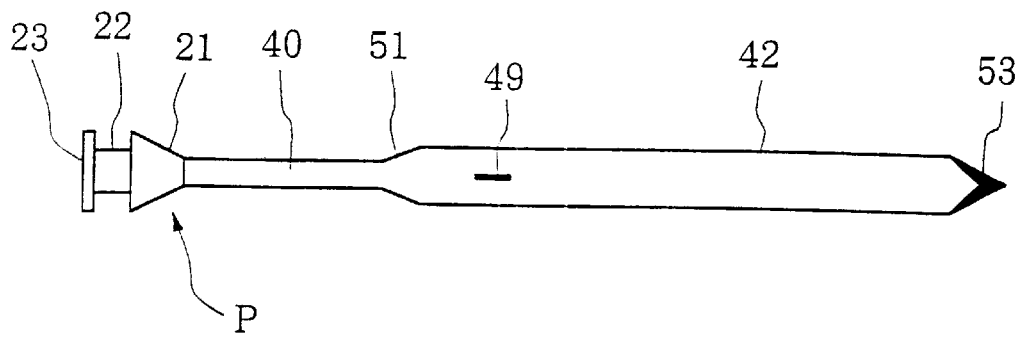
FIG. 12 is a schematic diagram showing an embodiment of the intubation device of the present invention.
Figure 13:
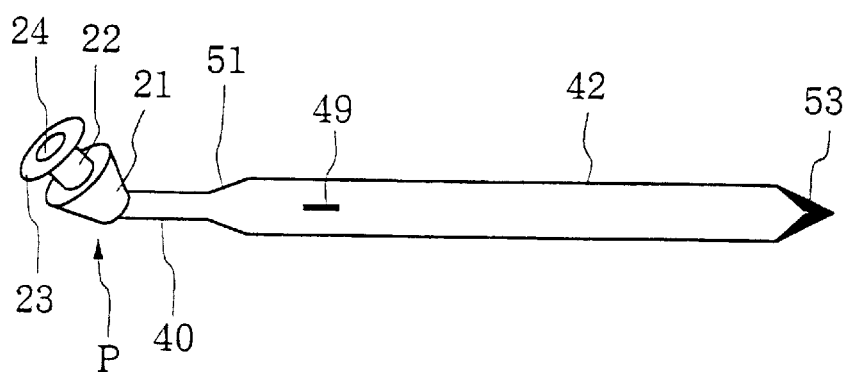
FIG. 13 is a schematic diagram showing another embodiment of the intubation device of the present invention.
Figure 14:
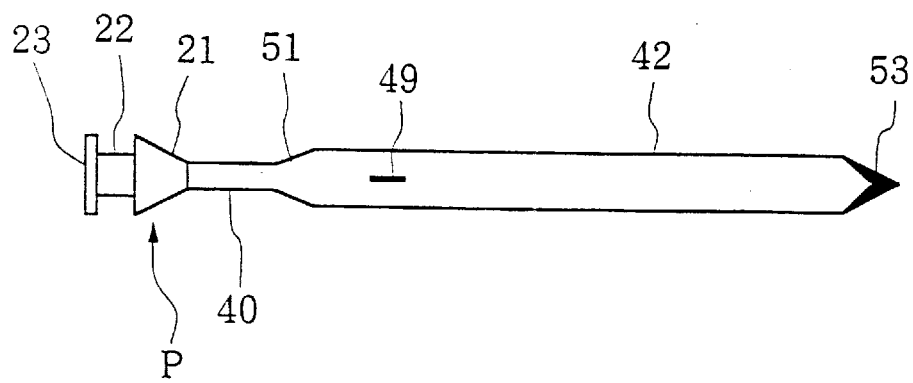
FIG. 14 is a schematic diagram showing yet another embodiment of the intubation device of the present invention.

FIGS. 12~14 show three different embodiments of this invention.

In the embodiments of FIGS. 12~14, the punctal plug P is attached to an end of the smaller soft tube 40, 1~15 mm in length, with silicone adhesive. The posterior end of the larger hard tube 42 is connected to the other end of the smaller tube 40. The tip 53 of the larger tube 42 is closed in a conical shape.

The punctal plug P consists of the conical portion 21 having a shape which is the frustum of a circular cone, and brim 23 having a circular elliptical shape and its whole body is a single piece. In the center of the brim 23, a hole 24 is formed. The hole 24 is connected with the lumen of the shaft 22, and the lumen of the tip 21, and connected with the inner space of the smaller tube 40 and the inner space of the larger tube 42 with a closed end (tip) 53.

In embodiments of FIG. 12 and FIG. 14, the axis of the smaller tube 40 is coincident with the axis of the larger tube 42 and the axis of the plug. Although in the embodiment of FIG. 13 the axis of the smaller tube 40 is coincident with the axis of the larger tube 42, the axis of the plug is not coincident with the axis of the smaller tube 40 and the axis of the larger tube 42 formed at a prescribed angle (for example 90~150°).

Although a plug without a hole 24 can be used and a rod can be used instead of smaller tube 40 in the embodiments of FIGS. 12~14, these embodiments are shown with hole 24 of the plug P connected with the closed end 53 via the lumen of the shaft 22, the inner space of the smaller tube 40, the inner space of the larger tube 42 and the lumen of the tip 21.

Regarding materials for tube 40, 42 and punctal plug P, it is important to select one which is substantially unstimulating and non-toxic to the tissue of the eye and body. From this point of view, silicone is appropriate because its safety is already established for apparatus for treatment of lacrimal duct obstruction. Above all, the combination of silicone tube 0.9~1.2 mm OD and 0.5~0.7 mm OD and 0.3~0.5 mm ID is especially preferred. Regarding punctal plug P, silicone punctal plugs are preferable as shown in FIGS. 12~14.

As shown in FIGS. 12~14, the right end of the smaller soft tube (0.5~0.7 mm OD, 0.3~0.5 mm ID, 2~20 mm in length, 40 is connected with the left end of the larger tube (0.9~1.2 mm OD, 0.5~0.7 mm ID, 5~50 mm in length) 42. The tip 53 of the larger tube 42 is sharp pointed and closed. For example, a 2 mm tip of the larger tube 42 is completely sealed with silastic adhesive, and then diagonally cut to taper the closed end 53. Small cuts 0.5 mm in length 49 for insertion of probe, 0.4 mm in length are formed in the larger tube 42 parallel to the tube 42. If the small cut is formed transverse to the tube, the tube may be broken during use. The preferred position of the small cut is 10 to 45 mm from the tip of the larger tube 42. The tube 42 can be easily inserted into the lacrimal duct by inserting the probe (not illustrated) from the small cut 49.

The preferred total lengths for the device of the present invention are as follows. A total length of 40~60 mm is appropriate for adult-nasolacrimal duct obstruction and a total length of 30~50 mm is appropriate for child-nasolacrimal duct obstruction. A total length of 10~60 mm is useful for reconstruction of canalicular obstruction and for use as a punctal plug.

The length and diameter of the silicone tube depend on the length and size of the inner space of the individual's lacrimal duct. The most commonly used is 51.7 mm in total length with the smaller tube 40 0.64 mm in diameter, 10 mm in length, the larger tube 42 0.94 mm in diameter, 40mm in length, and the punctal plug 1.7 mm in total length.

In order to be stable in the lacrimal duct, it is important that the smaller tube is softer. It is suitable as long as it is smaller in diameter and softer. For example a soft rod, without an opening, 0.5~0.7 mm in diameter can be used instead of the smaller tube 40.

It is better to make a taper 51 to avoid a step at the junction.

If the tip 53 of the larger diameter tube is sharp pointed in a conical shape, it is more easily inserted from the lacrimal puncta.

Figure 17:
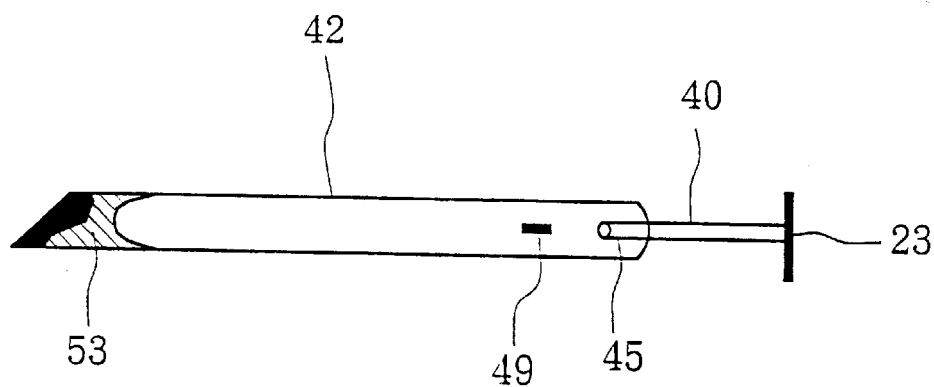
FIG. 17 is a schematic diagram showing yet another embodiment of the intubation device of the present invention.
Figure 18:
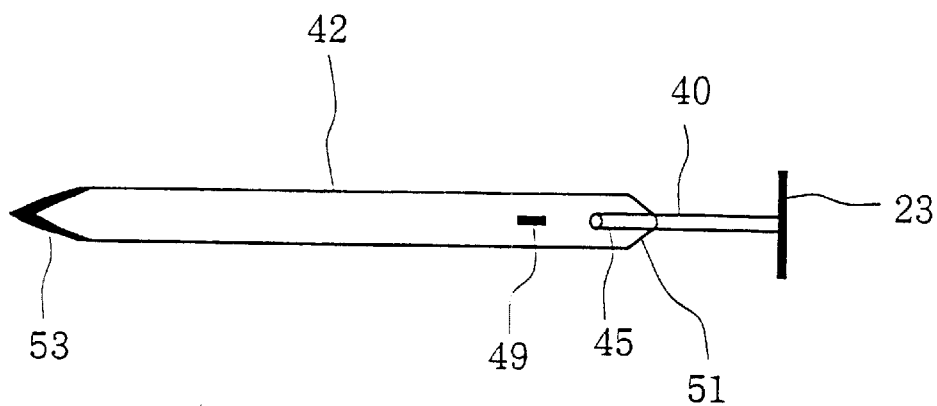
FIG. 18 is a schematic diagram showing still another embodiment of the intubation device of the present invention.

The devices of FIGS. 12~14 are of a one piece construction without junctions wherein the smaller tube 40 and the larger tube 42 are integrally formed. As shown in FIG. 17~18, it can be made by insertion of 2 mm of the end of the smaller tube into the larger tube and fixation using silicone glue. In the embodiment in FIG. 18, the junction between the smaller tube 40 and the larger tube 42 forms no step, and in the case of FIG. 17 the junction between the smaller tube 40 and the larger tube 42 is a step-like junction.

Although it is not illustrated, it is better for the tube to be equipped with the probe from the first.

The embodiments of FIGS. 8~11 are suitable for bicanalicular intubation in which a tube 40, 42, 41, 43 is introduced into the lacrimal duct from the upper and lower puncta. On the other hand, the embodiments of FIGS. 12~16 are suitable for monocanalicular intubation in which the intubation device is inserted into the lacrimal duct from the upper punctum only (or the lower punctum only).

Figure 15:
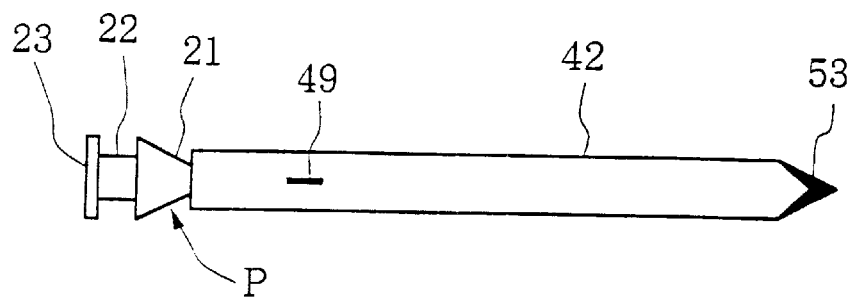
FIG. 15 is a schematic diagram showing still another embodiment of the intubation device of the present invention.
Figure 16:
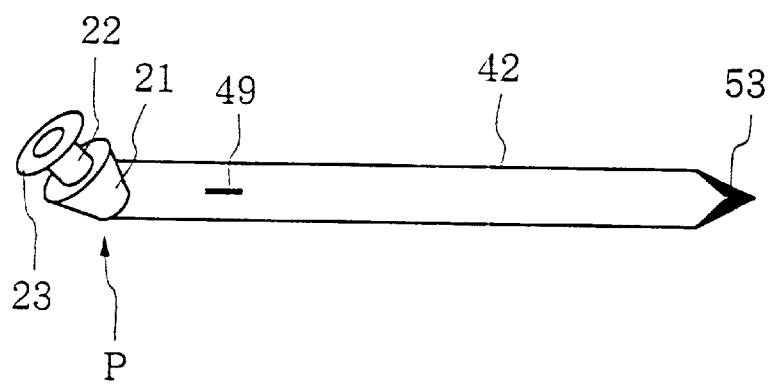
FIG. 16 is a schematic diagram showing another embodiment of the intubation device of the present invention.

In embodiment in FIG. 15 and FIG. 16, the punctal plug P is attached to the posterior end of the larger hard tube 42 with silicone glue without using the smaller soft tube. The tip 53 of the larger tube is in conical shape and closed. Punctal plug P is a one piece construction which consists of the tip 21 which has the shape of a frustum of a circular cone, the shaft 22 which is tubular, and the brim 23 which is circular. In the center of the brim 23 is formed hole 24. The hole 24 is connected with the lumen of the shaft 22 and the lumen of the tip 21 which is connected with the inner space of the larger tube 42 with a closed end 53.

The tube 42 can be easily inserted into the lacrimal duct by insertion of the probe (not illustrated) from the small cut 49 formed in the larger tube 42.

The embodiments of FIGS. 15~16 is superior for the treatment of the lacrimal duct obstruction. As shown in FIGS. 15~16, only the larger tube 42 is used and the smaller tube 40 is eliminated. The tip 53 of the larger tube 42 has a conical shape and is closed. When this tip 53 is inserted into the lacrimal duct from the upper punctum 1, the tube 42 is pushed into the lacrimal duct by the probe 61 (described later) which is inserted into the tube 42 to the tip 53. After insertion of the tube 42, the probe 61 is removed.

In the embodiment of FIG. 15, the axis of the larger diameter tube 42 is coincident with the axis of the plug P. Whereas, in the embodiment of FIG. 16, the axis of the plug P is not coincident with the axis of the larger tube 42 but, rather, is formed at a prescribed angle (for example 90~150°).

In the embodiment of FIG. 17, the brim 23 is joined with one end of the smaller soft rod 40 5~20 mm in length with silicone glue. The brim 23 is formed of a rather hard silicone.

In the embodiment of FIG. 18, the brim 23 is joined with one end of the smaller soft rod 40 5~20 mm in length, the brim 23 is formed of a rather hard silicone. The posterior end of the larger hard tube 42 is joined with the other end of the smaller tube 40. The tip 53 of the larger tube 42 is conical in shape and closed. The smaller rod 40 and the larger tube 42 are separately made and 2 mm of the end of the smaller rod is inserted into the larger tube for connection with silicone glue. This embodiment shown in FIG. 18 has no step at the junction between the smaller rod 40 and the larger tube 42.

Figure 19:
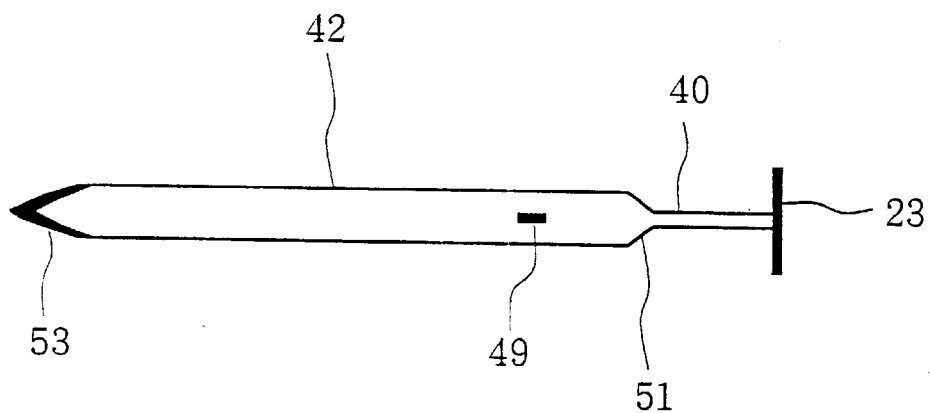
FIG. 19 is a schematic diagram showing a further embodiment of the intubation device of the present invention.

In the embodiment of FIG. 19, the brim 23 is joined with one end of the smaller soft tube 40 with silicone glue. The brim 23 is formed of a rather hard silicone. The posterior end of the hard tube 42 is joined with the other end of the smaller tube 40. The tip 53 of the larger tube 40 is conical in shape and closed. The smaller tube 40 is integral with the larger tube 42, i.e. one body. In the embodiment in FIG. 19, the junction between the smaller tube 40 and the larger tube 42 has no step.

Using the embodiment shown in FIG. 17~19, the tube 42 can be inserted into the lacrimal duct easily with a probe (not illustrated) which is inserted through the small cut 49 of the larger diameter tube 42.

Figure 20:
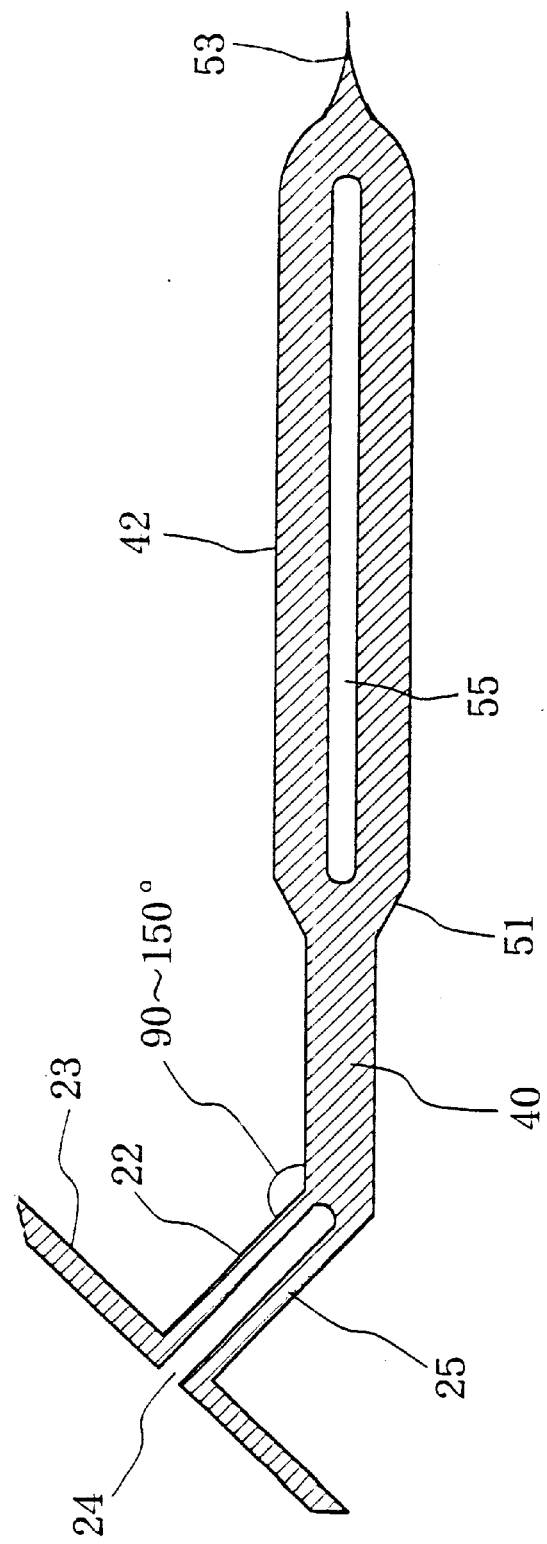
FIG. 20 is a cross-sectional view of an embodiment of the intubation device of the present invention.
Figure 21:
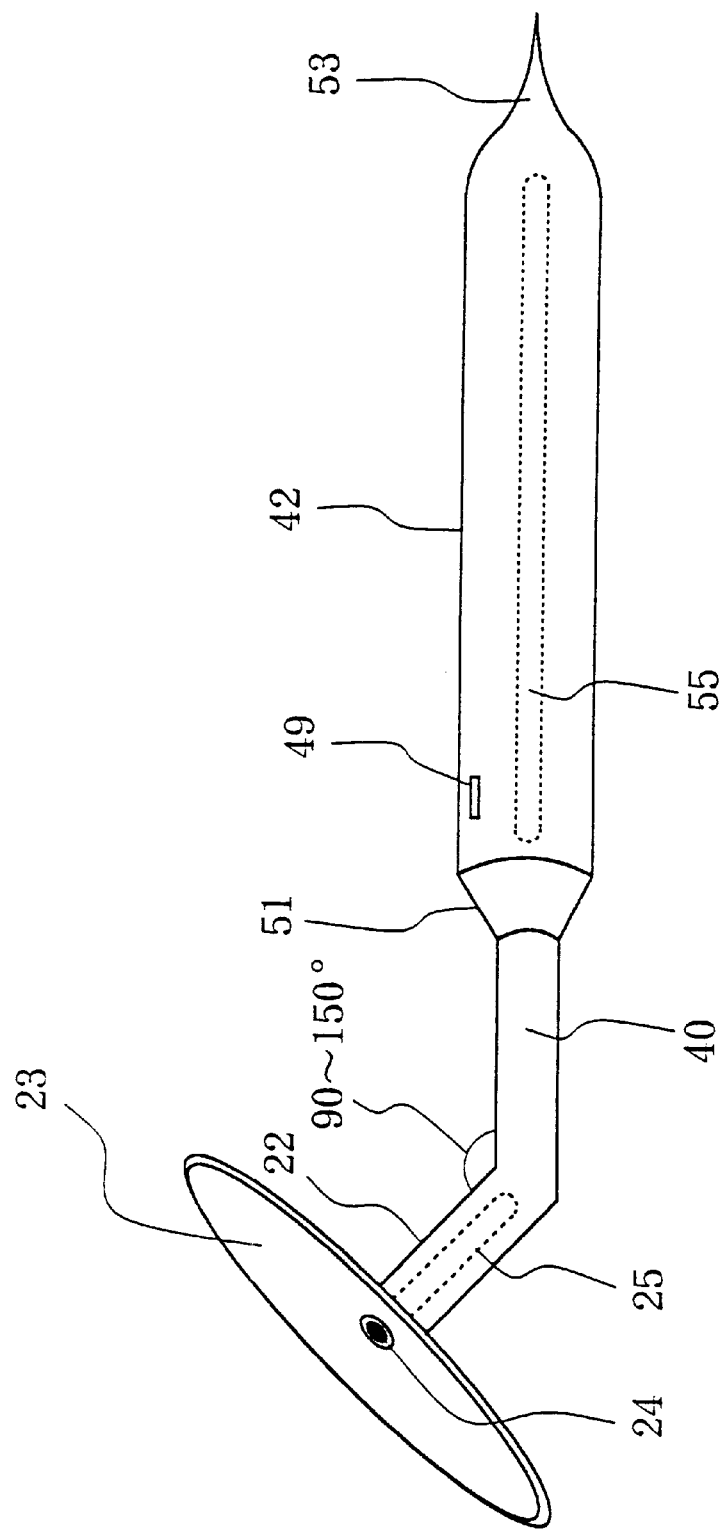
FIG. 21 is a perspective view of the embodiment of FIG. 20.

FIGS. 20~21 show other embodiments of the present invention. In these embodiments, the smaller diameter soft rod consists of the segment 22 0.5 mm OD and 2–2.5 mm in length, and the segment 40 0.5 mm OD and 3–20 mm in length. The segments 22, 40 join at an angle of 90~150 degrees. The brim 23 is joined with an end of the smaller diameter soft rod with silicone glue. The brim 23 is circular, elliptic or other shape, and formed of a hard silicone. The posterior end of the larger diameter hard tube 42 30–40 mm in length is joined integrally with the other end of the smaller diameter rod to form a single (unitary) body. The tip 53 of the larger diameter tube 42 is conical in shape and closed. The lumen 25 formed in the smaller diameter rod 22 is connected with the hole 24 in the brim 23. The lumen 25 extends into the smaller diameter rod to the aforementioned angle which exists in the middle of the smaller diameter rod. The larger diameter tube 42 1.0~1.2 mm OD and 0.5 mm ID has the lumen 55. The junction between the smaller diameter rod 40 and the larger diameter tube 42 tapered 51 without any step. And, in this embodiment, the axis of the brim 23 intersects the axis of the larger diameter tube 42 at a prescribed angle (for example 90~150 degrees).

The device of the embodiments of FIGS. 20~21 can be easily inserted into the lacrimal duct using a probe (not illustrated) which is inserted into the lumen 55 through the small cut 49 formed in the larger diameter tube 42.

Figure 22:
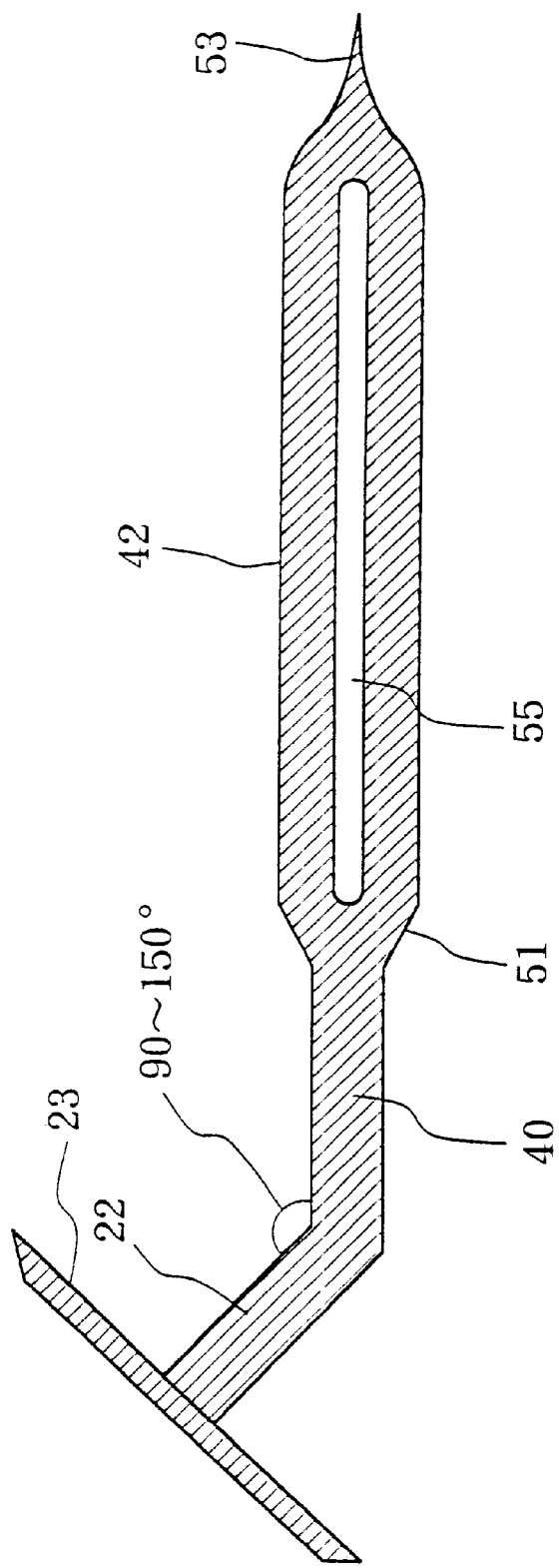
FIG. 22 is a cross-sectional view of another embodiment of the intubation device of the present invention.
Figure 23:
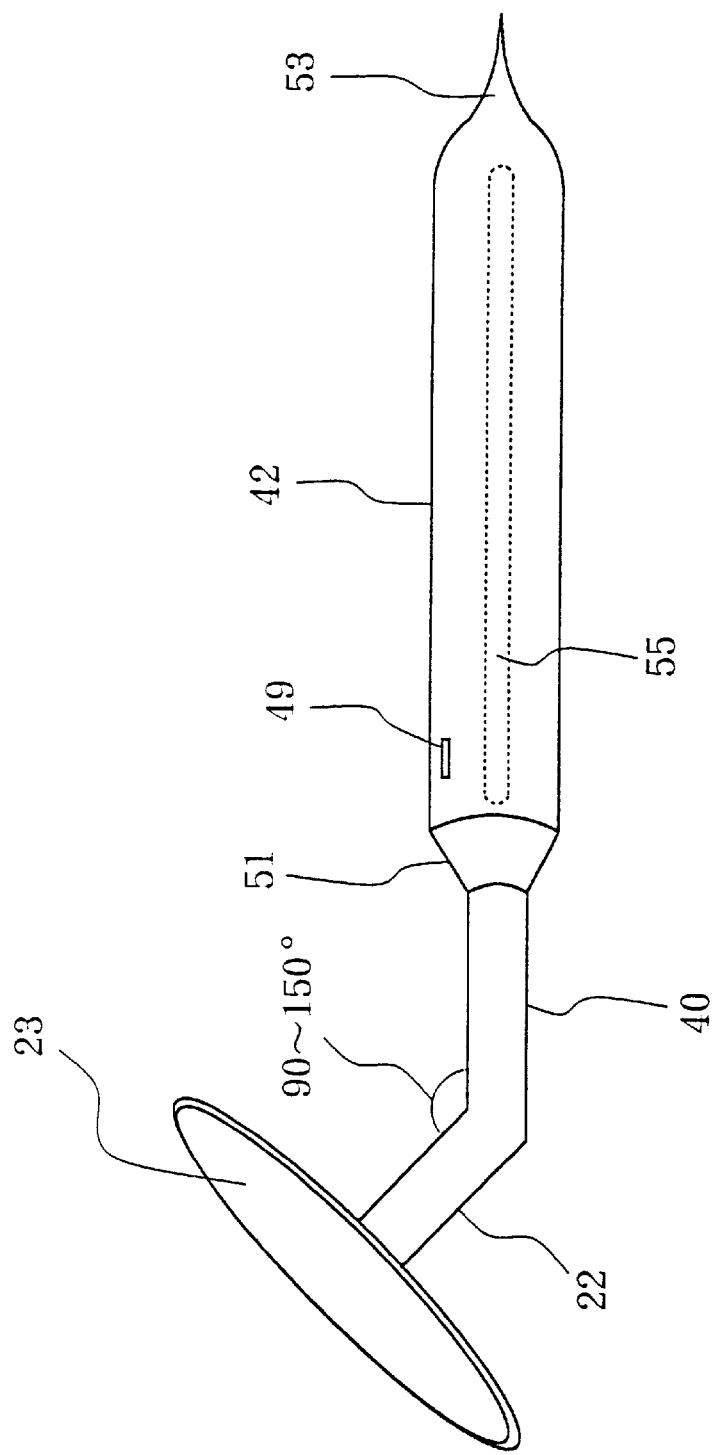
FIG. 23 is a perspective view of the embodiment of FIG. 22.

FIGS. 22~23 show another embodiment of the present invention wherein the smaller diameter soft rod is without a lumen and consists of the segment 22 0.5 mm OD, 1.5–2.5 mm in length and the segment 40 0.5 mm OD, 3–20 mm in length, and has a junction at an angle of 90~150 degrees between these segments 22, 40. The brim 23 is joined with an end of the smaller diameter soft rod with silicone glue. The brim 23 is circular elliptical or other shape and is formed of hard silicone. The posterior end of the larger diameter hard tube 42 30–40 mm in length is integrally joined with the other end of the smaller diameter rod to form a unitary body. The tip 53 of the larger diameter tube 42 is sharp pointed and has a closed end. The larger diameter tube 1.0~1.2 mm OD and 0.5 mm ID has a lumen 55 which extends to the closed end. The junction between the smaller diameter rod 40 and the larger diameter tube 42 is a taper 51, i.e. there is no step. And, in this embodiment, the axis of the brim 23 is set at a prescribed angle (for example 90~150 degrees) to the axis of the larger tube.

Using the device of the embodiments shown in FIGS. 20~21, the tube 42, can be easily inserted into the lacrimal duct with a probe (not illustrated) which is inserted through the small cut 49 formed in the larger diameter tube 42.

FIGS. 22~23 show other embodiments according to the present invention wherein the smaller diameter soft rod, without any lumen, consists of the segment 22 0.5 mm OD and 1.5–2.5 mm in length and the segment 40 0.5 mm OD and 3~20 mm in length, these segments 22, 40 joining at an angle of 90~150 degrees. The brim 23 is attached to an end of the smaller diameter soft rod with silicone glue. The brim 23 is circular elliptic, and is manufactured from hard silicone. The other end of the smaller diameter rod is connected to the posterior end of the larger diameter hard tube is connected to form one body. The tip 53 of the larger diameter tube is sharp pointed and closed. The larger diameter tube 42 is 1.0~1.2 mm OD and 0.5 mm ID, and lumen 55 extends to the closed end. The junction between the smaller diameter rod 40 and the larger diameter tube 42 has the taper 51 so as not to form any step. In this embodiment, the axis of the brim 23 is at a prescribed angle (for example 90~150 degrees) to the axis of the larger diameter tube 42.

Using the device of the embodiments shown in FIGS. 22~23, the tube 42 can be easily inserted into the lacrimal duct with a probe (not illustrated) which is inserted through the small cut 49 which is formed in the larger diameter tube 42.

Figure 24:
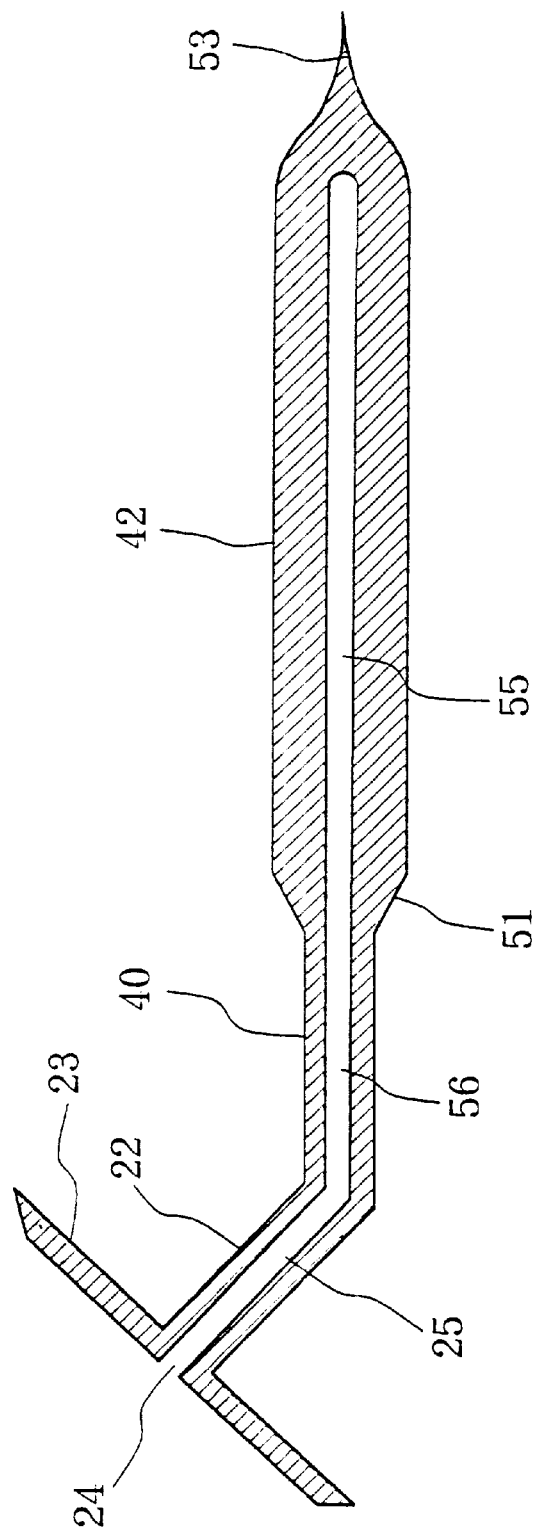
FIG. 24 is a cross-sectional view of yet another embodiment of the intubation device of the present invention.
Figure 25:
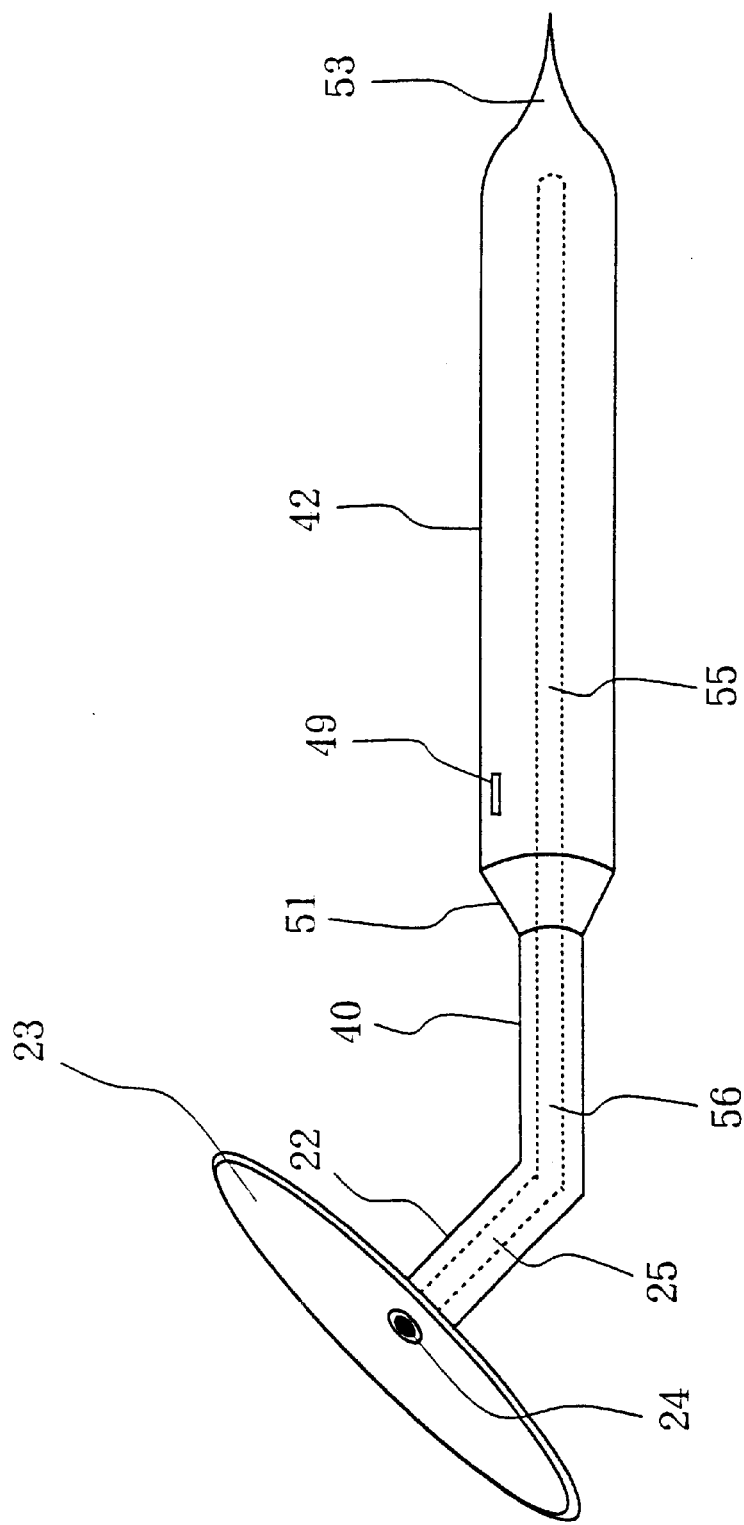
FIG. 25 is a perspective view of the intubation device of FIG. 24.

FIGS. 24~25 show other embodiments according to the present invention wherein the smaller diameter soft tube consists of the segment 22 0.5 mm OD and 214 2.5 mm in length and the segment 40, which segments 22, 40 join at an angle of 90~150 degrees. The brim 23 is attached to an end of the smaller diameter soft tube with silicone glue. The brim 23 is circular, elliptical of other form, and is manufactured from hard silicone. The posterior end of the larger diameter hard tube 42 30–40 mm in length, is connected with the other end of the smaller diameter tube to form a unitary body. The tip 53 of the larger diameter tube 42 is sharp pointed and closed. The lumen 25 in the smaller diameter tube 22 is connected with the hole 24 of the brim 23. The lumen 25 extends the total length of the smaller diameter tube. The larger diameter tube 42 has a 1.0~1.2 mm OD, a 0.5 mm ID and the lumen 55. The lumen 25 of the smaller diameter tube 40 is connected with the lumen 55. The junction is a taper 51, rather than a step. In this embodiment, the axis of the brim 23 is at a prescribed angle (for example 90~150 degrees) to the axis of the larger diameter tube 42.

Using the device of the embodiment shown in FIGS. 24~25, the larger diameter tube can be easily inserted into the lacrimal duct with a probe (not illustrated) which is inserted through the small cut 49 formed in the larger diameter tube 42.

Figure 26:
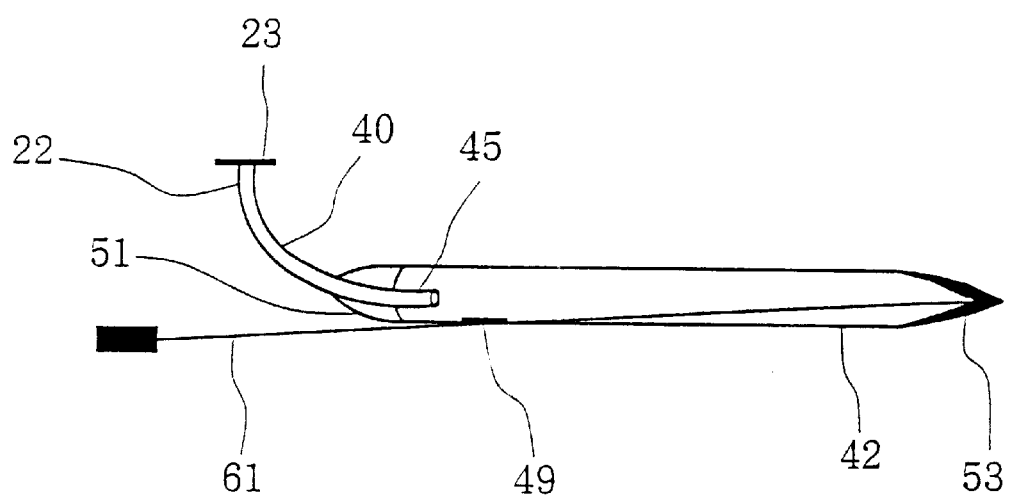
FIG. 26 is a perspective view showing the method of insertion of a device according to the embodiments of FIGS. 17~25.

FIGS. 26 shows still another embodiment according to the present invention wherein brim 23 is attached to an end of smaller diameter soft rod 40 with silicone glue. The brim 23 is circular, elliptical or other shape and is made of hard silicone. Into the posterior end of the larger diameter tube, is inserted the smaller diameter rod 40 to join them. The segment of the smaller diameter rod 22 curves from junction 45 to the brim 23. The junction 45 is formed as a taper without any step. And in this embodiment, the axis of the brim 23 is at a prescribed angle (for example, 90~150 degrees) to the axis of the larger diameter tube 42. Thus, the embodiment shown in FIG. 26 is substantially the same as the embodiments FIGS. 20–25, and the tube 42 can be easily pushed into the lacrimal duct by the probe 61 which is inserted into the lumen 55 from the small cut 49 in the larger diameter tube 42.

Figure 27:
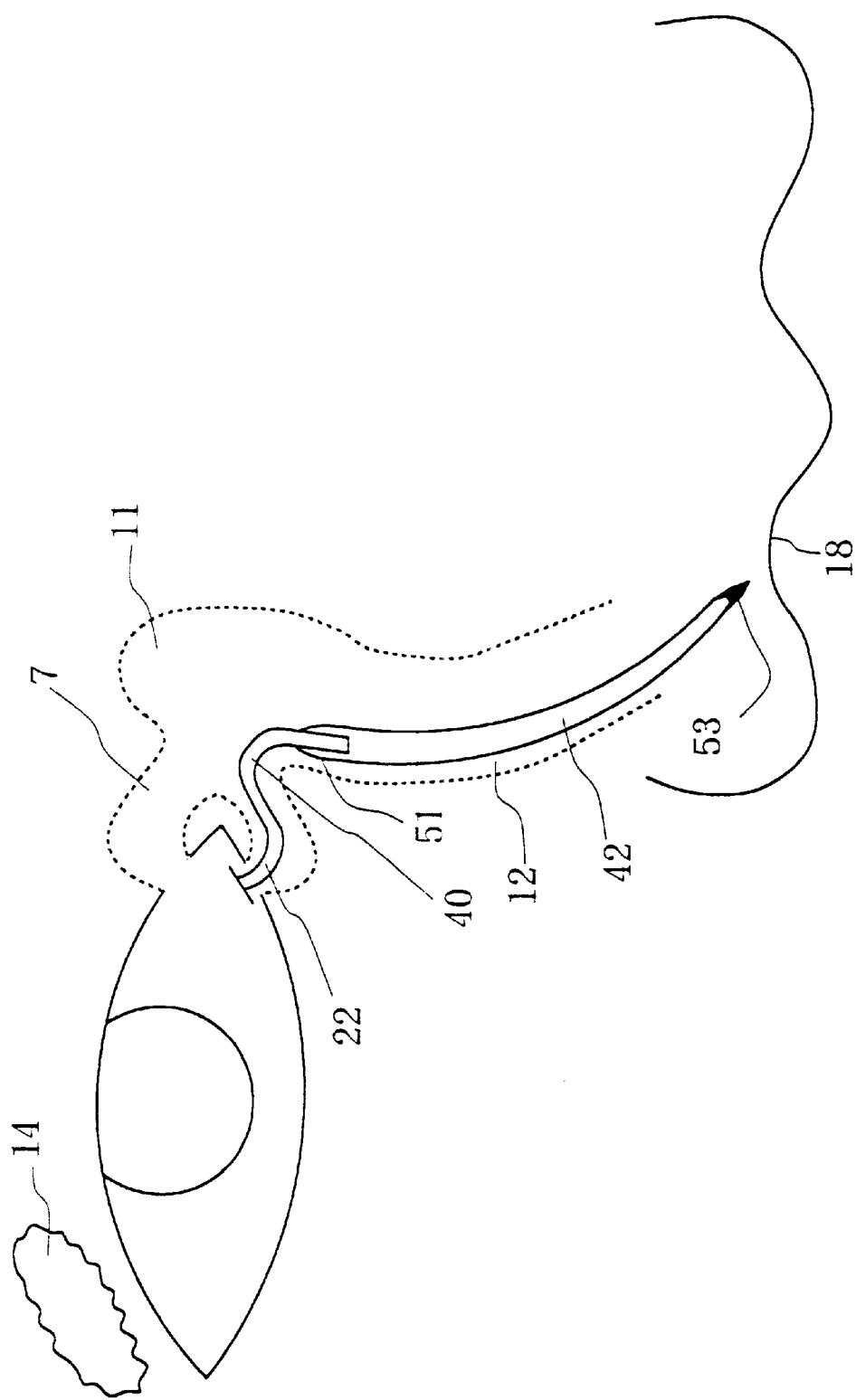
FIG. 27 is a diagram showing a monocanalicular intubation method using a device in accordance with the embodiments of FIGS. 17~25.

FIGS. 27 shows a post-operative state of placement of the intubation device of an embodiment of FIGS. 20–26 inserted from the lower canaliculus.

Figure 28:
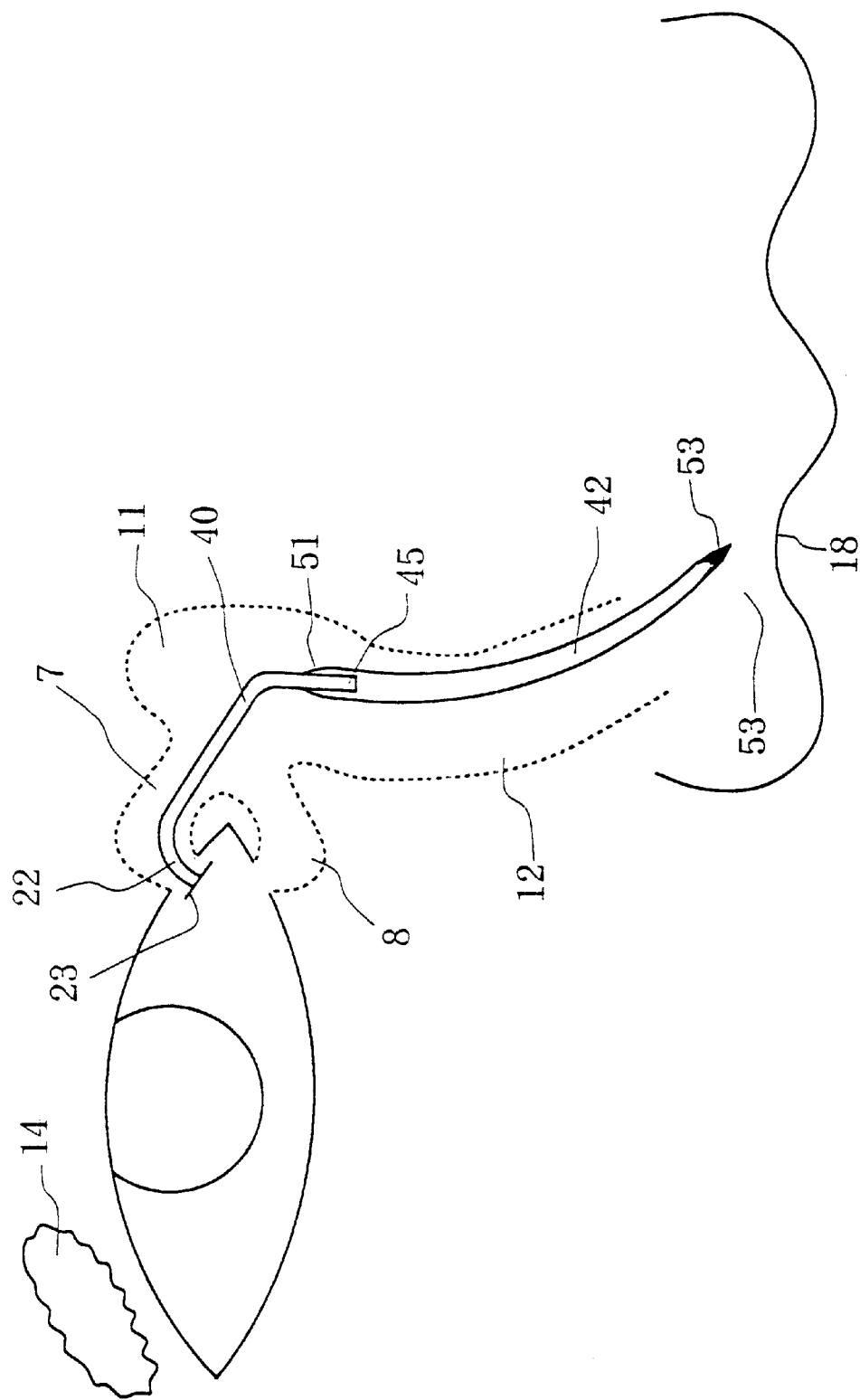
FIG. 28 is a diagram showing another monocanalicular intubation method using a device in accordance with FIGS. 17~25.

FIG. 28 shows a post-operative state of placement of the intubation device of an embodiment of FIGS. 20–26 inserted from the upper canaliculus.

Figure 29:
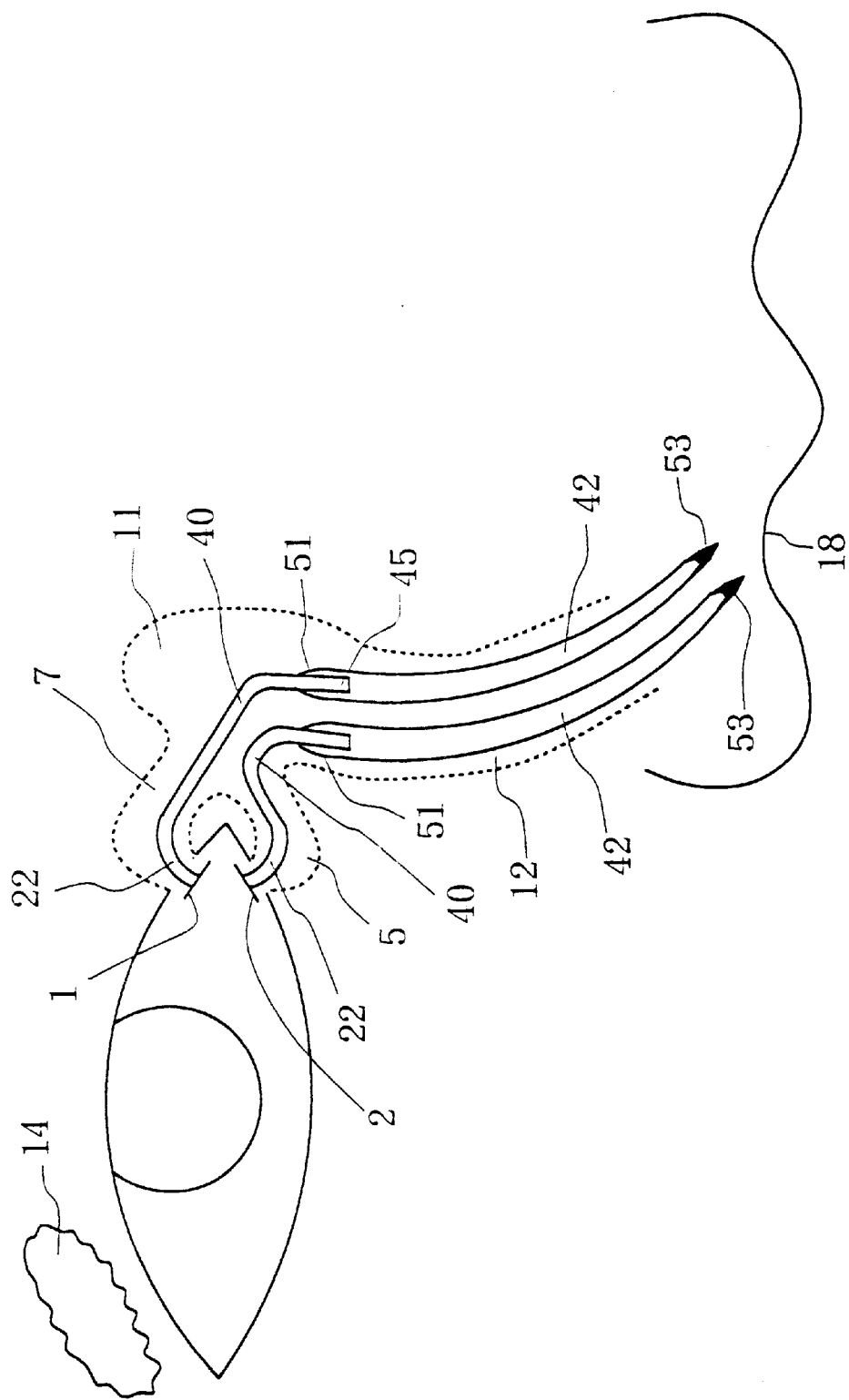
FIG. 29 is a diagram showing a bicanalicular intubation method using a device according of FIGS. 17~25.

FIGS. 29 shows a post-operative state of placement of an intubation device of FIGS. 20–26 inserted from the upper and lower canaliculi. This is the most suitable placement for the treatment of dry eye.

Figure 30:
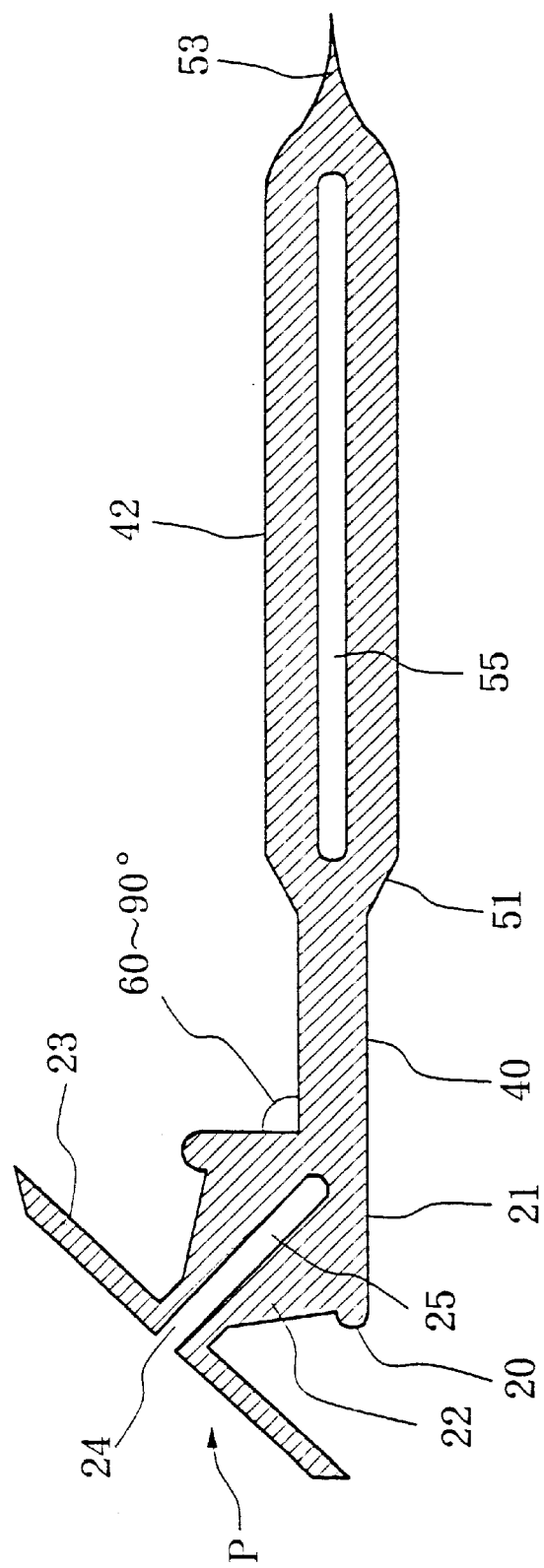
FIG. 30 is a sectional view of yet another embodiment of the intubation device of the present invention.
Figure 31:
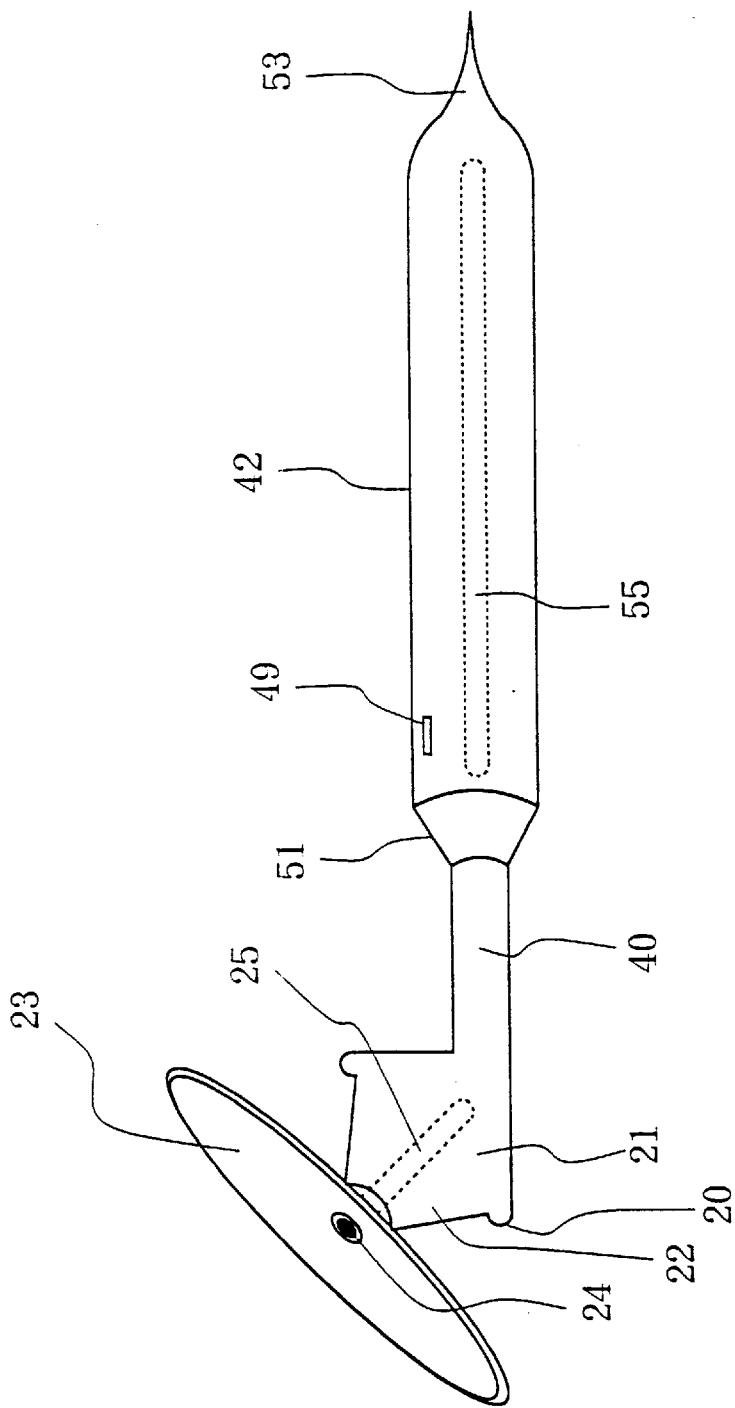
FIG. 31 is a perspective view of the embodiment of FIG. 30.

FIGS. 30–31 show still another embodiment of the present invention. The punctal plug P is attached to an end of the smaller diameter soft rod 40. The punctal plug P consists of the tip 21, intermediate portion 22 and the brim 23. The edge 20 is round so as not to induce granulation. The brim 23 is circular, elliptical or other shape and is made of hard silicone. The posterior end of the larger diameter hard tube 30~40 mm in length is connected with the other end of the smaller diameter rod to form one body. The tip 53 of the larger diameter tube 42 is sharp-pointed and closed The lumen 25 in plug P is connected with the hole 24. The larger diameter tube 42 has lumen 55, an outer diameter of 1.0~1.2 mm, and an inner diameter of 0.5 mm. The junction is tapered so as not to form a step. And, in these embodiments also, the axis of the brim 23 is at a prescribed angle (for example 90~50 degrees) to the axis of the larger diameter tube 42.

Using a device of one of the embodiments of FIGS. 30–31 also, the larger diameter tube 42 can be easily inserted into the lacrimal duct with a probe 61 which is inserted into the lumen 55 from the small cut 49 in tube 42.

Figure 32:
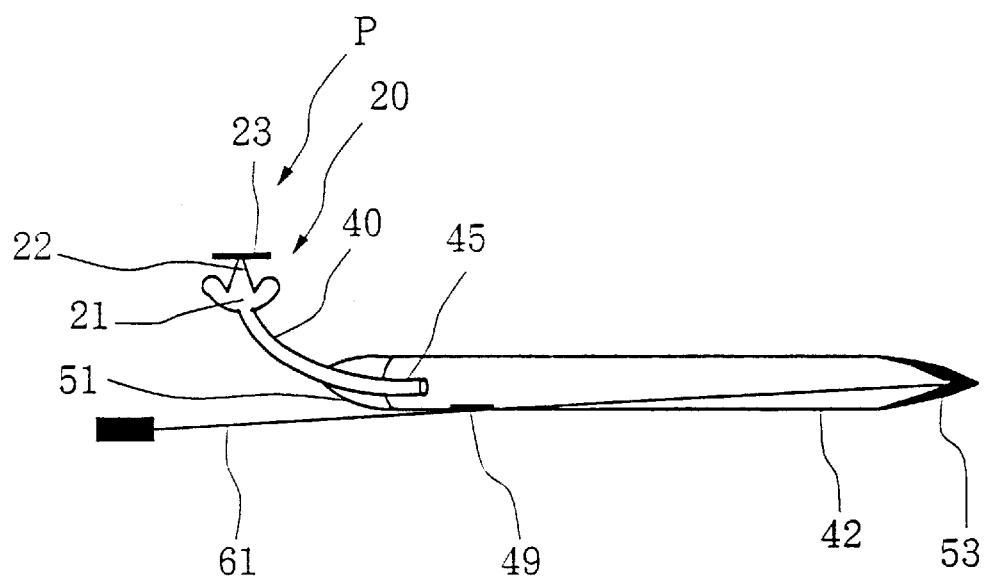
FIG. 32 is an explanatory diagram showing an insertion method for use of the intubation device of FIGS. 30~31.

FIGS. 32 shows one manner of insertion of a device in accordance with FIGS. 30–31.

Figure 33:
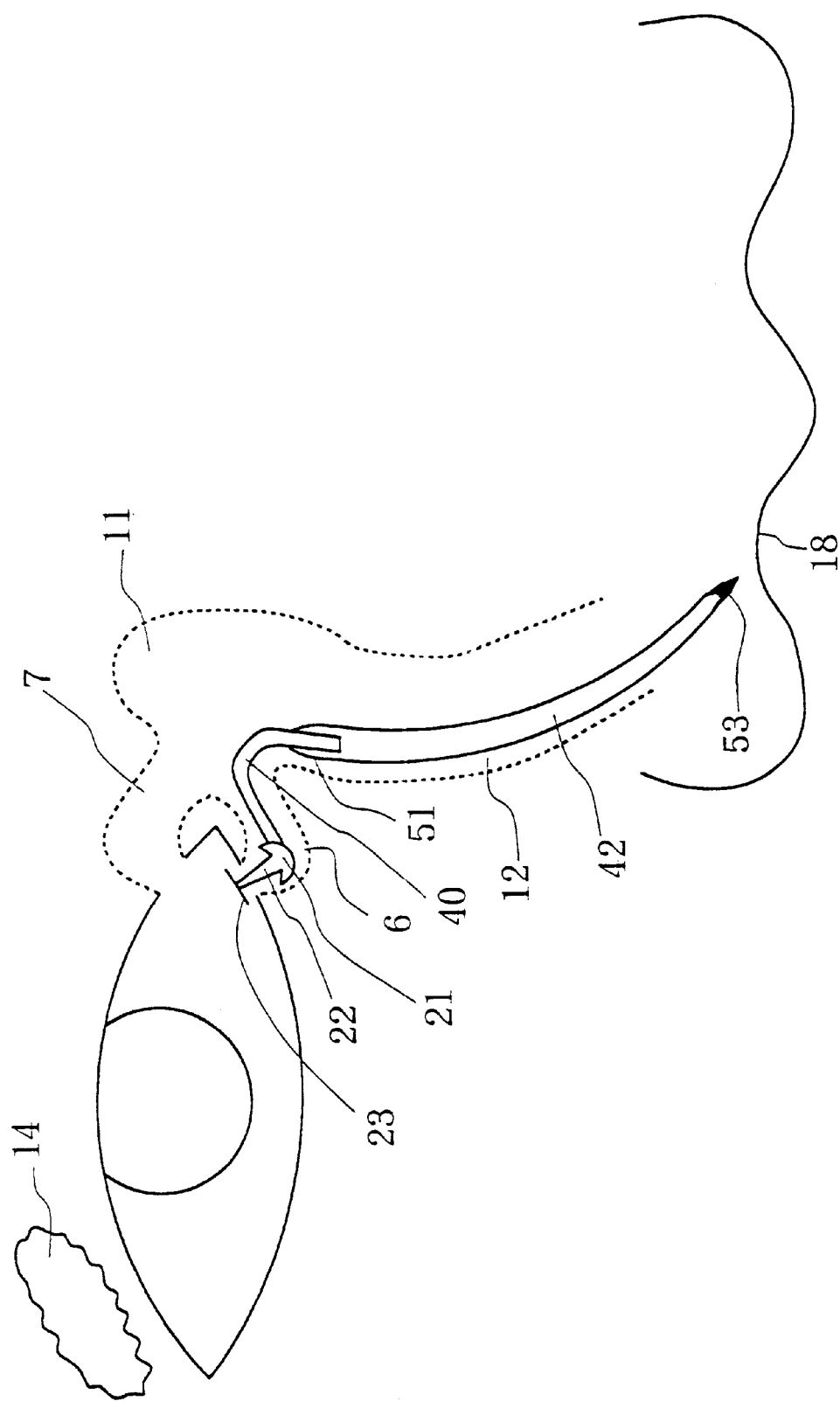
FIG. 33 is an explanatory diagram showing a monocanalicular intubation method using the intubation device of FIGS. 30~31.

FIG. 33 shows a post-operative state of placement of a device for intubation of the present invention, in accordance with the embodiments in FIGS. 30–31, inserted from the lower canaliculus.

Figure 34:
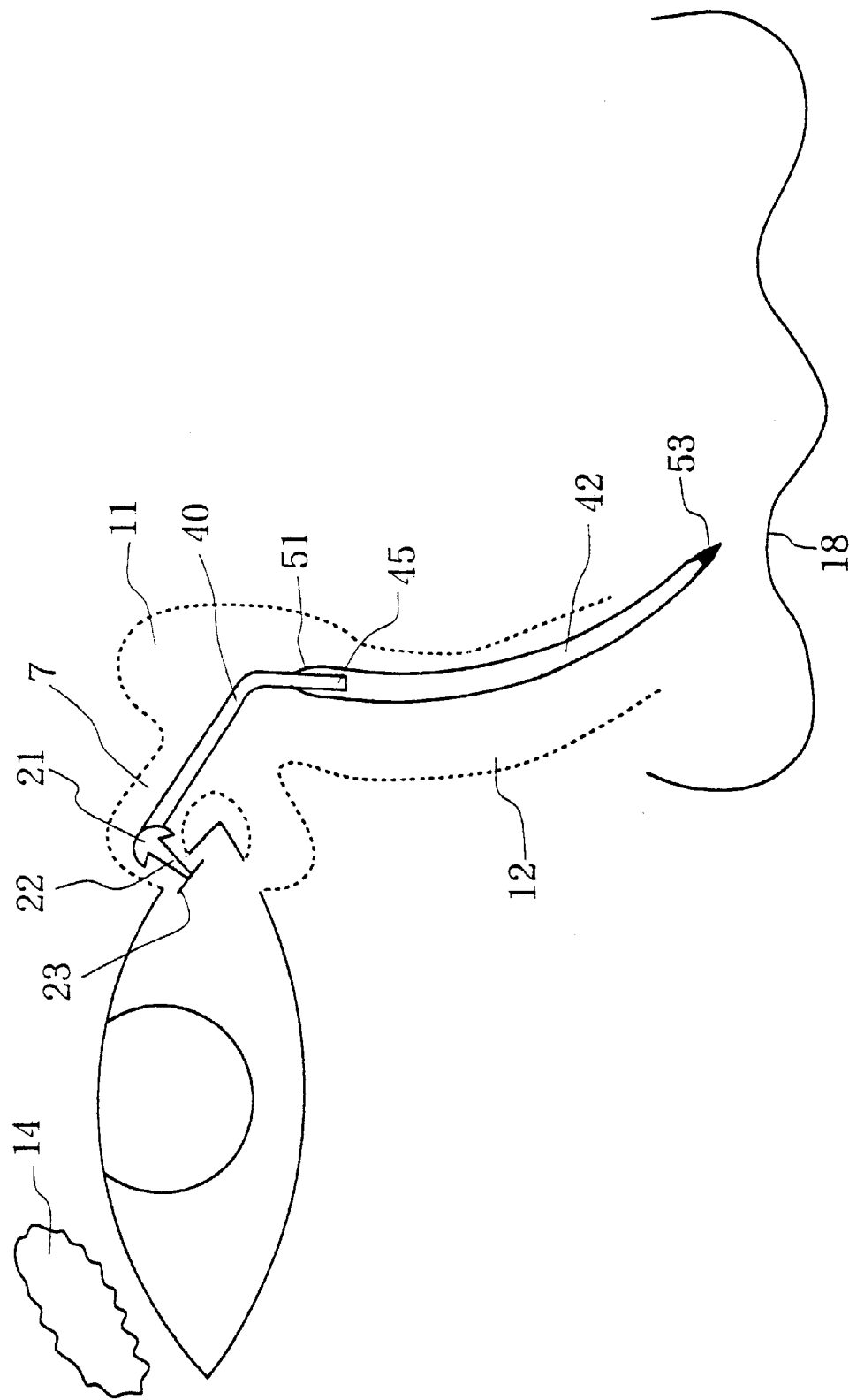
FIG. 34 is an explanatory diagram showing another monocanalicular intubation method using the intubation device of FIGS. 30~31.

FIG. 34 shows a post-operative state of placement of a device for intubation of the present invention, in accordance with the embodiments in FIGS. 30–31, inserted from the upper and lower canaliculi.

Figure 35:
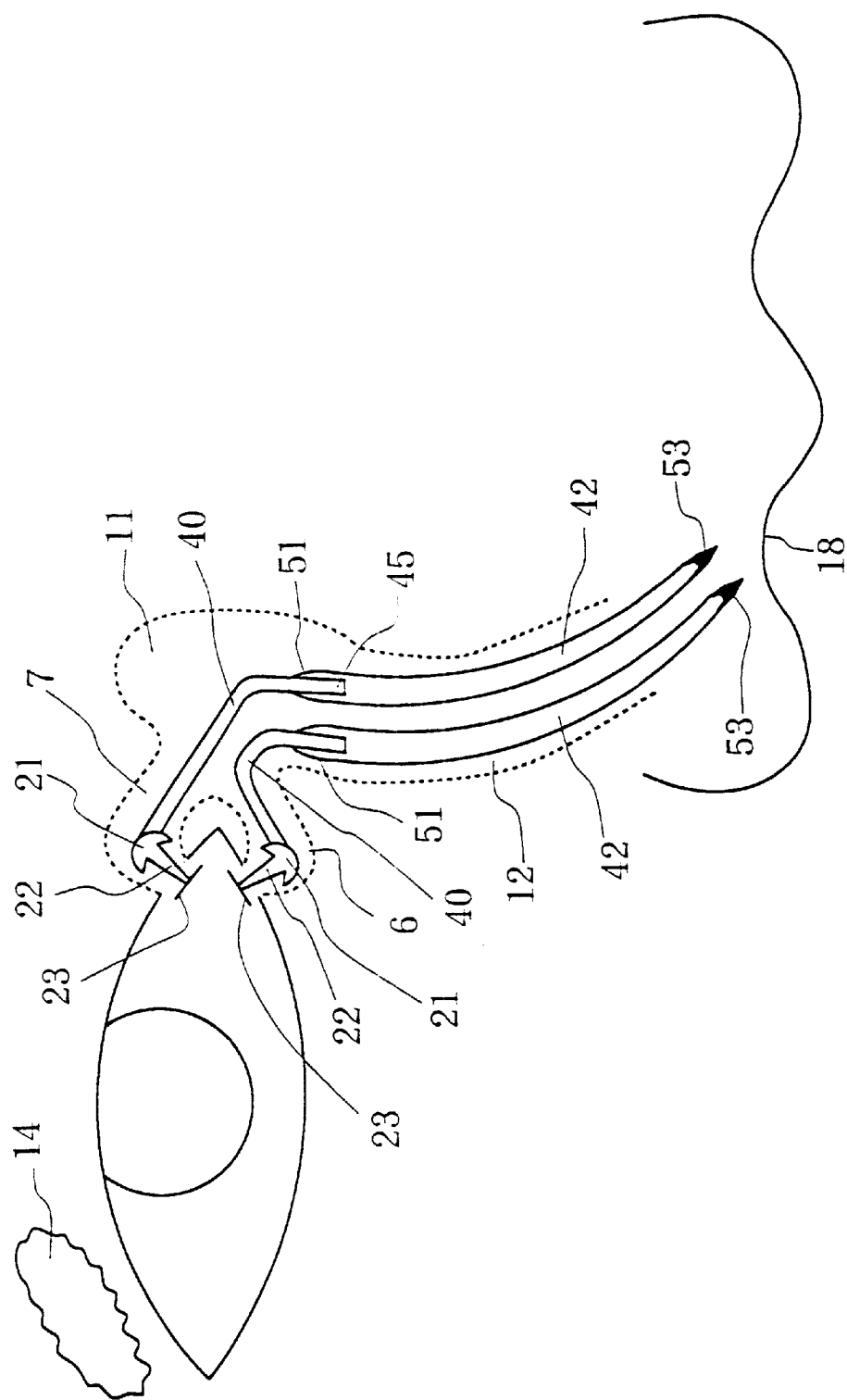
FIG. 35 is an explanatory diagram showing a bicanalicular silicone intubation method using the intubation device of FIGS. 30~31.

FIG. 35 shows a post-operative state of placement of an intubation device of the present invention, in accordance with the embodiments in FIGS. 30–31, inserted from the lower canaliculus.

In many cases, insertion in one of the upper and lower puncta is sufficient to prevent epiphona. Therefore it is preferred to place the device for intubation of the present invention in the lower or upper canaliculus after opening of obstructed portion(s) of the lacrimal duct.

Figure 36:
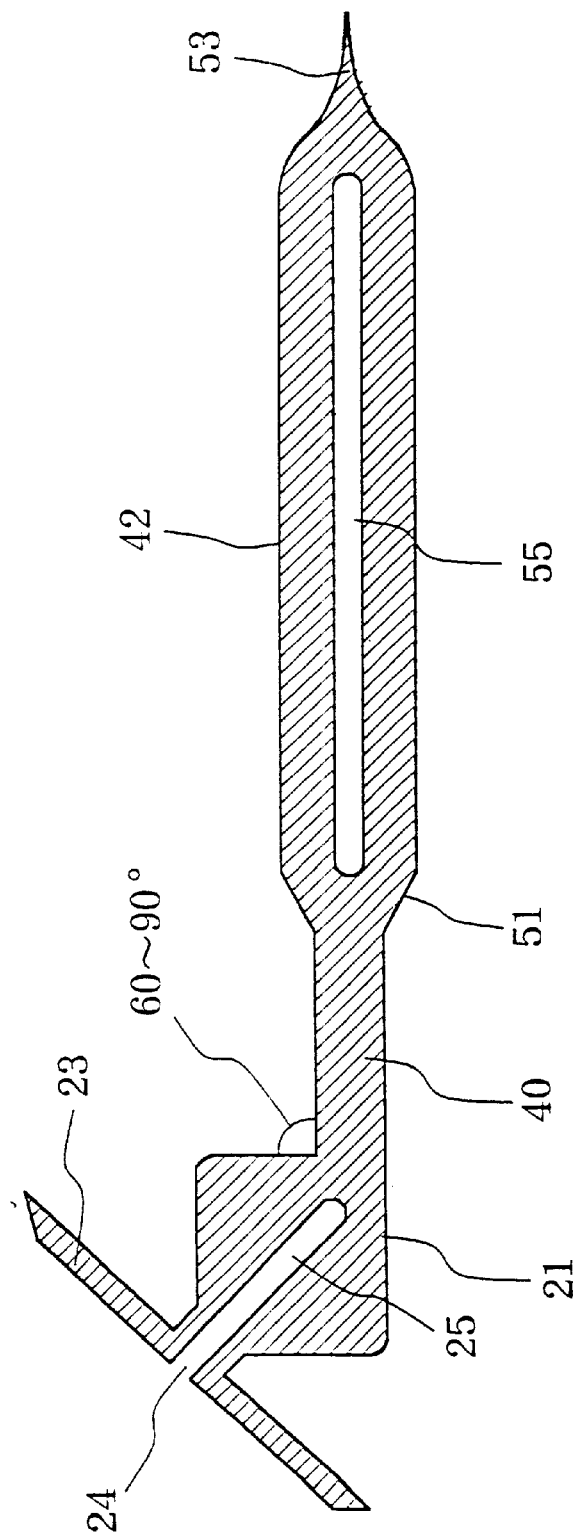
FIG. 36 is a cross-sectional view showing another embodiment of the intubation device of the present invention.
Figure 37:
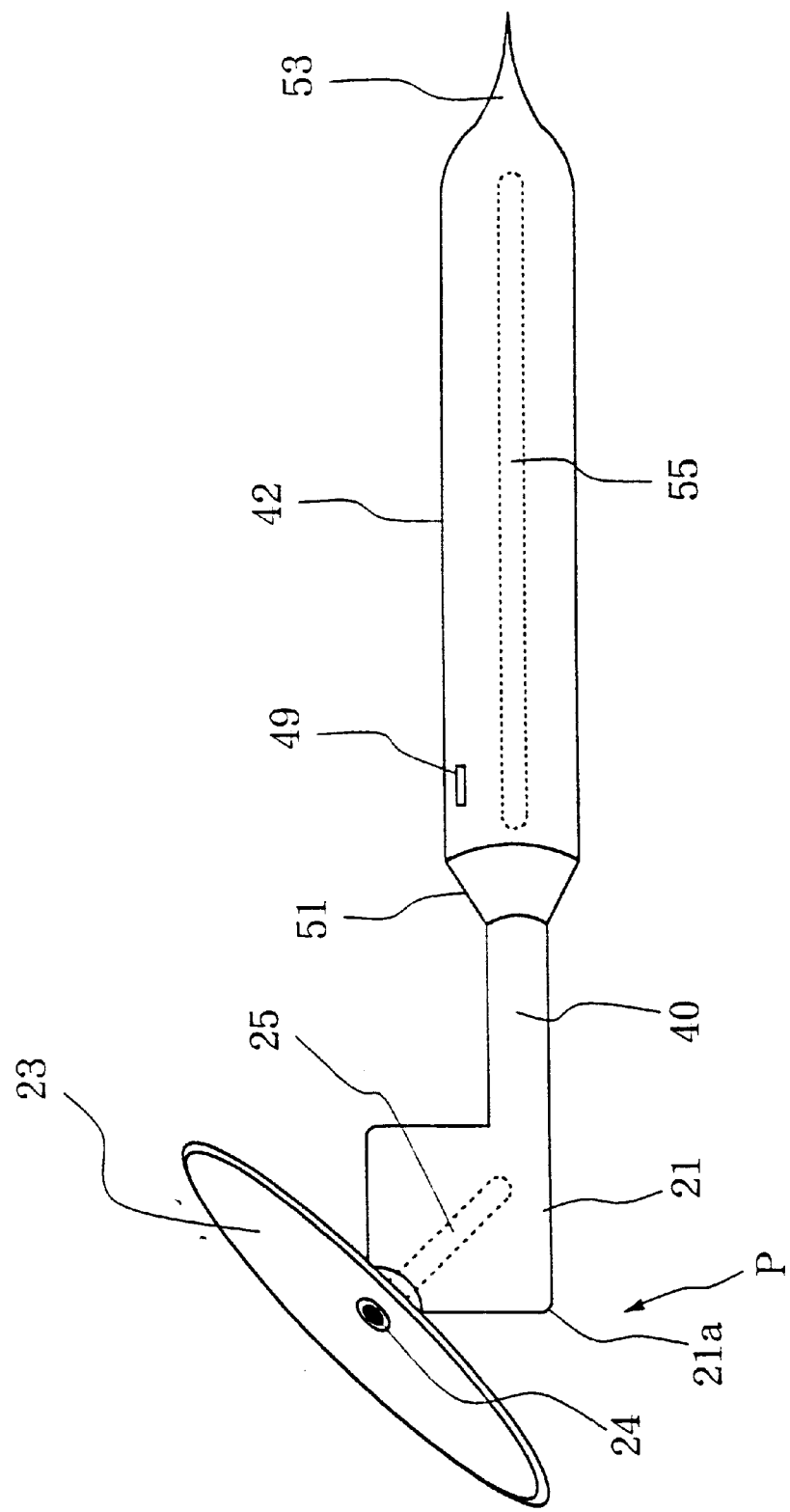
FIG. 37 is a perspective view of the intubation device of FIG. 36.

FIGS. 36~37 show additional embodiments wherein the punctal plug P is attached to an end of the smaller diameter soft rod. The punctal plug P consists of the tip 21 and the brim 23. The edge 21a of the tip 21 is round so as not to induce granulation. The brim 23 is circular, elliptical, or other shape and is made of hard silicone. The posterior end of the larger diameter hard tube 42 is connected with the other end of the smaller diameter rod 40 as to form one body. The tip 53 of the larger diameter tube 42 is sharp-pointed and closed. The lumen 25 of the plug P is connected with the hole in the brim 23. The lumen 55 is present in the larger diameter tube which has a 1.0~1.2 mm OD and a 0.5 mm ID. The junction 51 between the smaller diameter rod 40 and the larger diameter tube 42 is tapered so as to avoid forming a step. And in this embodiment also, the axis of the brim 23 is at a prescribed angle (for example 90~150 degrees) to the axis of the larger diameter tube 42.

The tube 42 of the embodiment of FIGS. 36~37, can be pushed into the lacrimal duct by a probe 61 which is inserted into the lumen 55 through the small cut 49 in the larger diameter tube 42.

Figure 38:
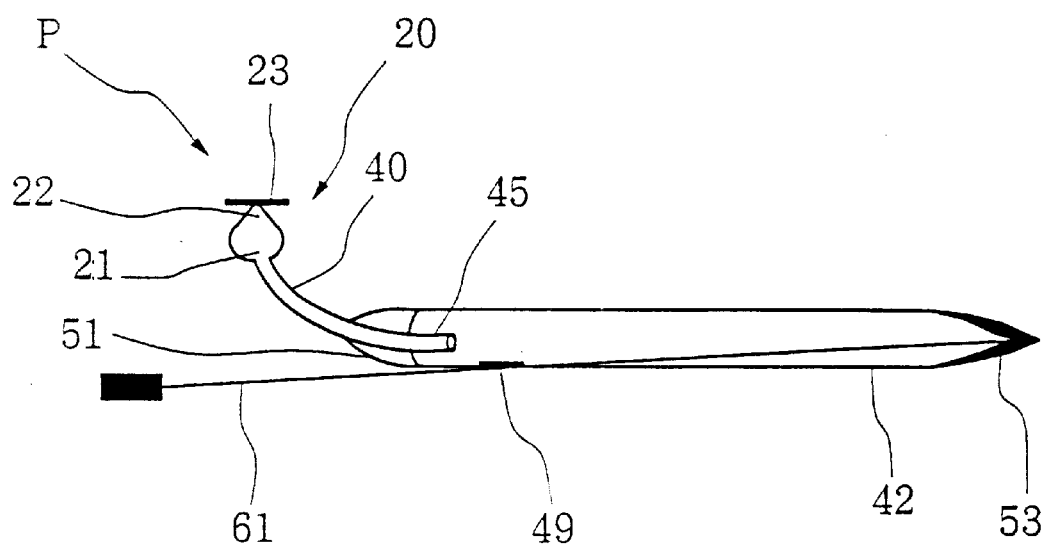
FIG. 38 is an explanatory diagram showing a method of insertion of the intubation device of FIGS. 36~37.

FIG. 38 shows one manner of insertion of the device of the embodiment of FIGS. 36~37.

Figure 39:
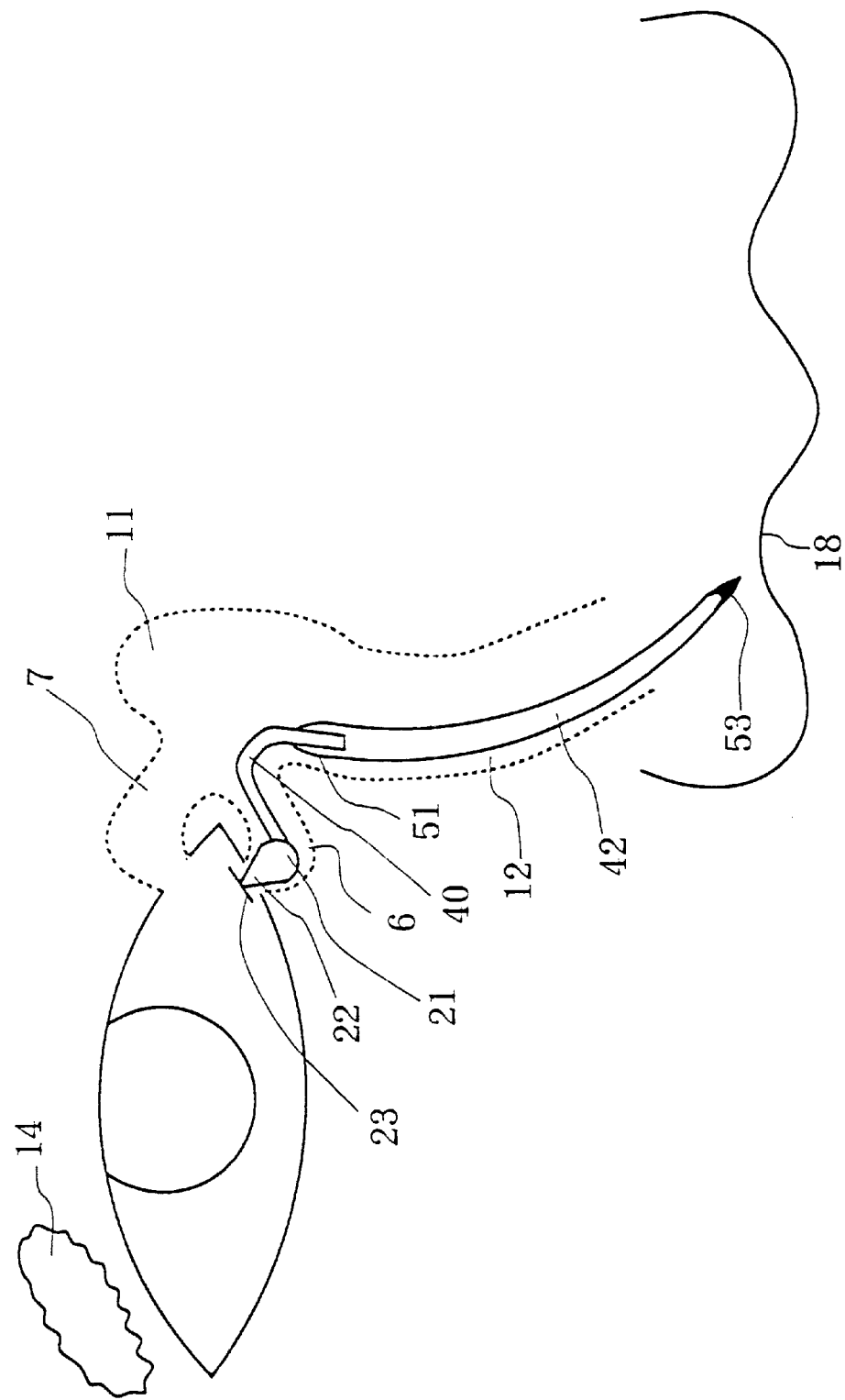
FIG. 39 is an explanatory diagram showing a monocanalicular silicone intubation method using the device of FIGS. 36~37.

FIG. 39 shows a post-operative state of placement of the device of the embodiment of FIGS. 36~37.

Figure 40:
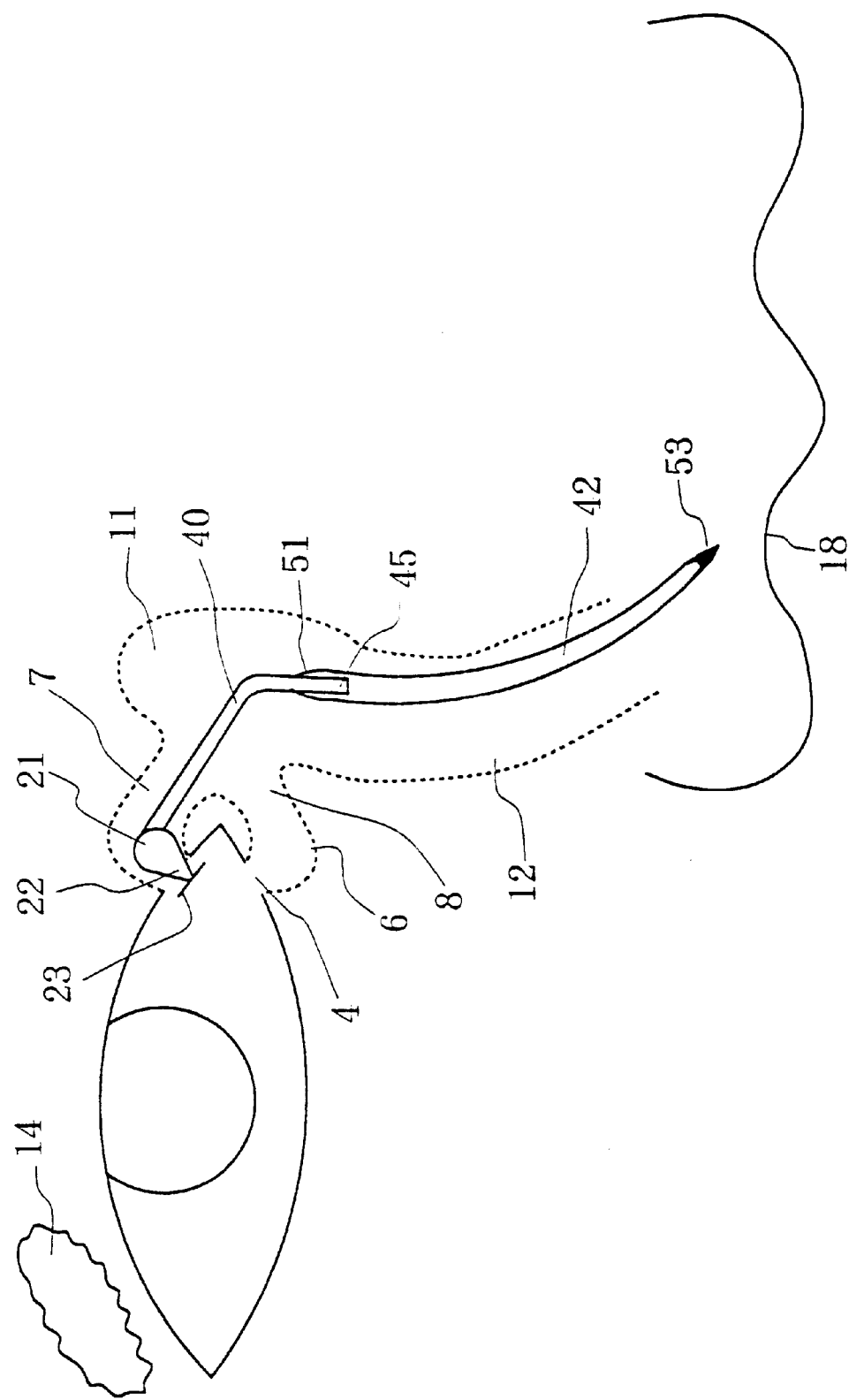
FIG. 40 is an explanatory diagram showing another monocanalicular silicone intubation method using the intubation device of FIGS. 36~37.

FIG. 40 shows a post-operative state of placement of the device of the embodiment of FIGS. 36–37 inserted from the upper canaliculus.

Figure 41:
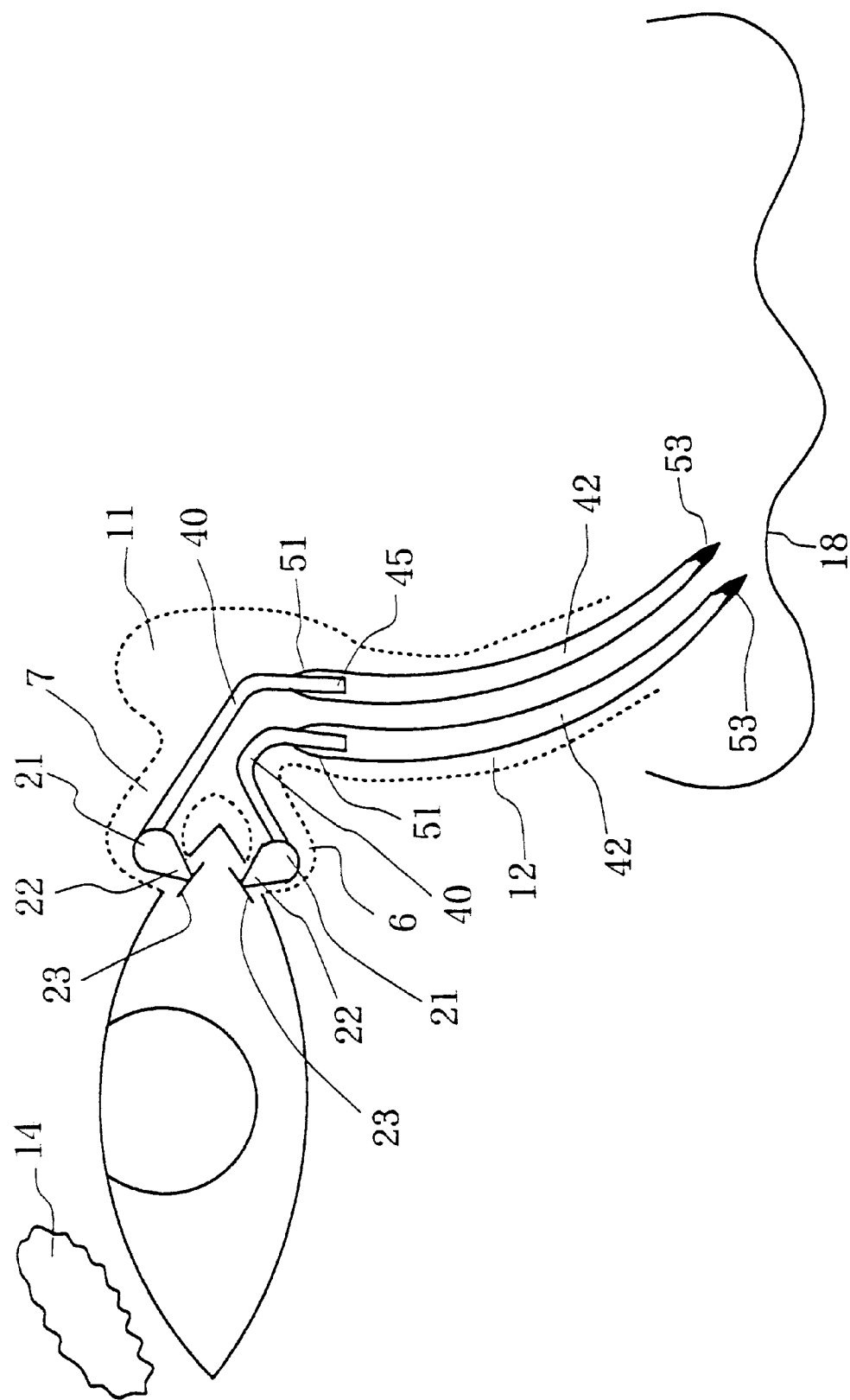
FIG. 41 is an explanatory diagram showing a bicanalicular intubation method using the intubation device of FIGS. 36~37.

FIG. 41 shows a post-operative state of placement of the device of the embodiment of FIGS. 36–37 inserted from the upper and lower canaliculi.

Insertion in one of the upper and lower canaliculi is sufficient to prevent epiphora. Therefore, it is preferred to place the device for intubation of the present invention in the lower or upper canaliculus, after opening of obstructed portion(s) of the lacrimal duct.

Figure 42:
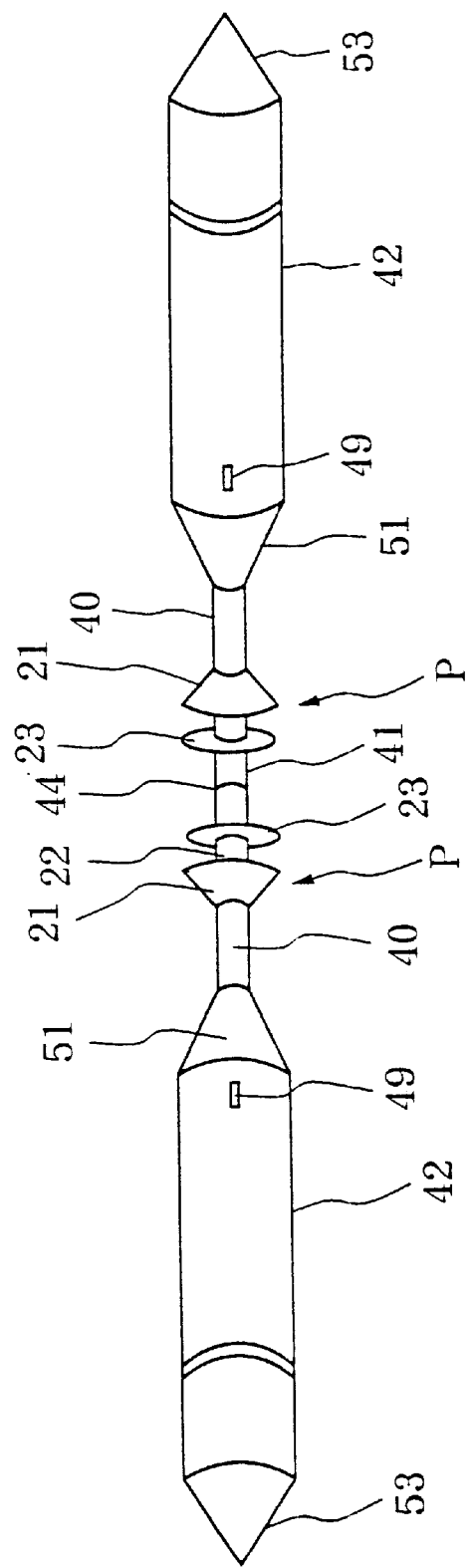
FIG. 42 is a perspective view showing still another embodiment of the intubation device of the present invention.
Figure 43:
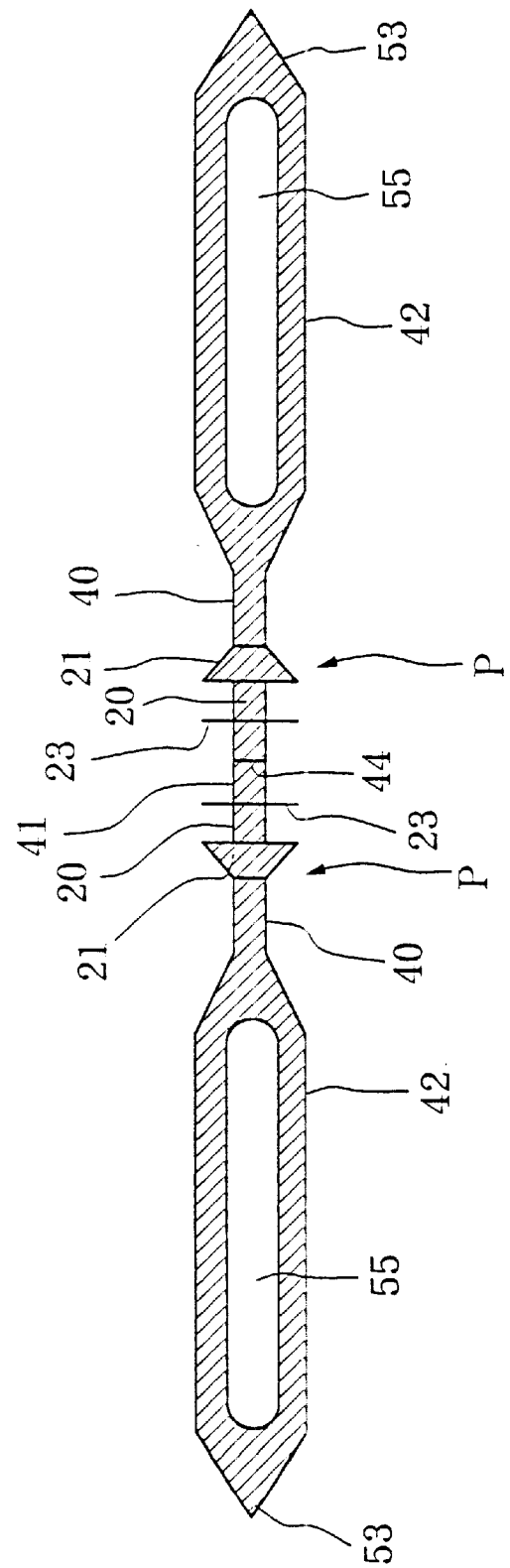
FIG. 43 is a mid-cross sectional view of the intubation device of FIG. 42.

FIGS. 42~43 show still other embodiments of the present invention.

The device for intubation of the lacrimal duct shown in FIGS. 42~43, has two smaller diameter soft rods 40 and two larger diameter tubes 42 to be inserted into the lacrimal duct. The free (distal) end of each larger diameter tube 42 is closed. Between the two larger diameter tubes 42, are two smaller diameter rods 40 exist and another smaller diameter rod 41 is located between the two smaller diameter rods 40, and the midpoint of the additional rod 41 has a marking 44. The junction 51 between the smaller diameter rod 46 and the larger diameter tube 42 is tapered so as to avoid forming a step. The tip 53 of the larger diameter tube 42 is conical in shape.

A punctal plug P is positioned between each of the two smaller diameter soft rods 40 and the additional rod 41. Each punctal plug P consists of the tip 21, shaft 22 and brim 23. The brim is circular, elliptical or other shape and is made of hard silicone. The plug P has no lumen. The larger diameter tubes each have a lumen 55, an outer diameter of 1.0~1.2 mm and an inner diameter of 0.5 mm. The junction 51 between each smaller diameter rod 40 and larger diameter tube 42 is tapered without any step.

The tube 42 of the embodiment of FIGS. 42~43, can be easily pushed into the lacrimal duct by a probe 61 which is inserted into the lumen through the small cut 49 in the larger diameter tube 42.

Figure 44:
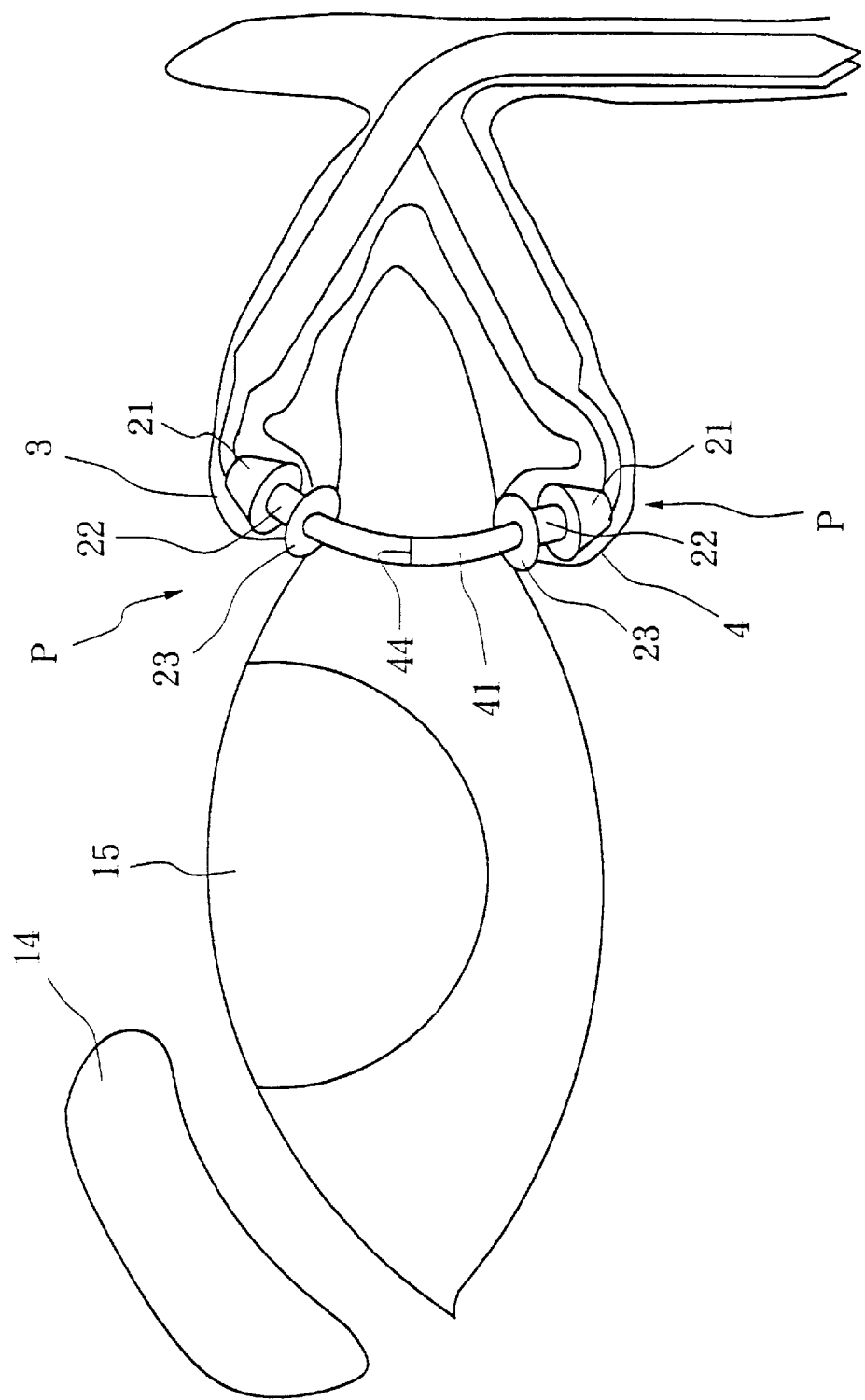
FIG. 44 is an explanatory diagram showing a method of placement of the intubation device of FIGS. 42~43.

FIG. 44 shows one method of insertion of the device of the embodiment shown in FIGS. 42–43 from the upper and lower canaliculi.

Finally, the general method of surgery using the device for intubation according to the present invention will be explained.

Before insertion, the obstructed segment(s) of the lacrimal duct is opened by insertion of probe 61. And in advance, the puncta are dilated by punctal incision at their lateral wall or using a punctal dilator. The tip 53 of the tube 42 enclosing the probe 0.4 mm in diameter 61 is pushed into the inferior nasal meatus from the lower punctum 2 via the lower canaliculus 4, 6, 8, common canaliculus 9, lacrimal sac 11 and nasolacrimal duct 12. Then, the intubation device is left in place and the probe 61 is removed.

Next, if necessary, another intubation device is pushed into the lacrimal duct from the upper punctum 1 and in advance, the probe 61 0.5–1 mm in diameter is inserted from the upper punctum 1. The upper punctum is also dilated by punctal incision at the lateral wall or by using a punctal dilator. The tip 53 of the tube 42 is pushed into the inferior nasal meatus by the probe 61 which inserted into the larger diameter tube through the small cut in the same way.

The intubation device can be easily removed by holding and pulling the plug P, brim 23 or smaller diameter rod 41 at the upper punctum 1 and the lower punctum 2 using forceps.

Although any of the devices for intubation of the present invention is usually used under local anesthesia or general anesthesia using an operating microscope, it can be more simply used with many patients under local anesthesia.

Silicone is preferred for making the apparatus for intubation according to the present invention. Silicone is unstimulating and non-toxic to the living body so it is possible to leave it in place for a long time.

Unlike the prior art, the intubation device according to the present invention does not require a difficult nasal procedure at all, resulting in short operating time and a small burden on patients.

Unlike the prior art tubes, it has the stopper and can be bent, to make the tube stable in the lacrimal duct inhibiting easy migration. Furthermore, patients feel very little pain.

Although it is easy to insert the intubation device according to the present invention into the lacrimal duct and easy to remove it, it is not easily dislocated during the intubation period.

A combination of larger and smaller diameter tube or rod segments is preferred.

The small cuts formed in the larger diameter tube do not break the tube.

The tube with a sharp-pointed tip and conical in shape can be easily intubated into the lacrimal duct after punctal dilation, with only punctal dilator (without punctal incision).

The ease of intubation of the lacrimal duct with the device of the present invention makes it possible for doctors to do intubation routinely before resorting to major surgical intervention.

The intubation device of the present invention is less easily dislocated compared to the prior art punctal plug when used for the treatment of dry eye.

Furthermore, the following advantages can be gained according to the present invention:

1) It is unnecessary to fix the device with suture(s) in monocanalicular intubation.

2) Incidence of granulation due to stimulation by the angular portions of the prior punctal plug is decreased by rounding the angular portion of the device of the present invention.

3) Obstruction between the vertical portion and the horizontal portion of canaliculus is not induced. Furthermore, it is useful as a stent in treatment of canalicular obstruction and nasolacrimal duct obstruction.

4) By making the brim of the punctal plug elliptical, the brim can be enlarged so as not to stimulate the ocular surface and to prevent the plug from migrating into the canalicular.

5) By making the tip of the larger diameter tube sharp-pointed, it can be easily inserted from the punctum.

6) Tear fluid cannot enter into the punctum because blocked by the brim which adheres to the puncta because the larger tube is pulled into the lacrimal duct.

7) Punctal occlusion and the treatment of lacrimal duct obstruction and dacryocystitis can be performed simultaneously for patients with dry eye, lacrimal duct obstruction and dacryocystitis.

8) Positioning of the smaller diameter soft tube between the punctal plug and the larger diameter tube stabilizes the intubation device in the lacrimal duct. Furthermore, making an angle of 90°–150° between the axes of the punctal plug and the larger diameter tube makes it more stable.

9) Attachment of the brim to only the smaller diameter tube also makes it more stable.

What is claimed is:

1. A device for intubation of the lacrimal duct comprising: a smaller diameter tube or rod having a prescribed length, a larger diameter tube having a prescribed length and extending from one end of said smaller diameter tube or rod, and a stopper attached to the other end of said smaller diameter tube or rod, wherein said larger diameter tube has a central lumen, a slit for insertion of a probe into the central lumen and a tip which is sharp-pointed and closed and forms one distal end of the device.

2. A device as defined in claim 1 wherein said stopper is a punctal plug having a diameter larger than said larger diameter tube.

3. A device as defined in claim 1 wherein said stopper is a brim in the form of a flange of a diameter larger than that of said larger diameter tube.

4. A device as defined in claim 1 wherein said stopper is a ring.

5. A device as defined in claim 1 wherein said larger diameter tube defines a central axis, and said stopper has an axis which is at an angle of 90–150 degrees to the central axis of said larger diameter tube.

6. A device as defined in claim 1, wherein said larger diameter tube has a central axis, and said small cut runs parallel to the central axis of said larger diameter tube.

7. A device as claimed in claim 1 wherein the stopper includes a disk larger than the diameter of the larger diameter tube.

8. A device as claimed in claim 7 wherein the stopper further includes a frusto-conical portion and a neck portion joining said disk to said frusto-conical portion.

9. A device as claimed in claim 7 wherein said stopper has a central lumen opening through a hole in said disk, wherein said smaller diameter tube rod is a tube with a central lumen and wherein said larger diameter tube has a central lumen in communication with the hole through the lumen in the smaller diameter tube and the stopper.

10. A device as claimed in claim 9 wherein said larger diameter tube is longer than said smaller diameter tube.

11. A device as claimed in claim 1 wherein said larger diameter tube is longer than said smaller diameter tube.

12. A device for intubation of the lacrimal duct comprising: a tube having a prescribed length, and a stopper attached to a posterior end of said tube, wherein said larger diameter tube has a central lumen, a slit for insertion of a probe into the central lumen and a tip which is sharp-pointed and closed and forms one distal end of the device.

13. A device as defined in claim 2 wherein said stopper is a punctal plug having a diameter larger than the diameter of said tube.

14. A device as defined in claim 2 wherein said stopper is a brim in the form of a flange of a diameter larger than the diameter of said tube.

15. A device as defined in claim 2 wherein said stopper is a ring.

16. A device as defined in claim 2 wherein said tube defines a central axis and said stopper has an axis which is at an angle of 90~150 degrees to the central axis of said tube.

17. A device as claimed in claim 16 wherein the stopper further includes a frusto-conical portion and a neck portion joining said disk to said frusto-conical portion.

18. An apparatus as defined in claim 2, wherein said tube has a central axis, and said small cut runs parallel to the central axis of said tube.

19. A device as claimed in claim 2 wherein the stopper includes a disk larger than the diameter of the tube.

20. A device for intubation of the lacrimal duct comprising:

A smaller diameter tube or rod;

a pair of stoppers spaced apart and symmetrically arranged in said smaller diameter tube or rod, on opposing sides of a midpoint of said smaller diameter tube or rod, each of said stoppers having a circumferential disk extending radially from said smaller diameter tube or rod; and a larger diameter tube connected to each of opposing ends of said smaller diameter tube or rod, each larger diameter tube having a central lumen, a slit for insertion of a probe into the central lumen and a distal end which is sharp-pointed and closed.

* * * * *